US012653475B2

(12) United States Patent
Doi et al.

(10) Patent No.: US 12,653,475 B2
(45) Date of Patent: Jun. 16, 2026

(54) ANGULAR DEVIATION CALIBRATION OF IVUS AND OCT DURING ENDOSCOPY

(71) Applicant: TERUMO KABUSHIKI KAISHA, Tokyo (JP)

(72) Inventors: Yukiko Doi, Fujinomiya (JP); Masanori Tokida, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 167 days.

(21) Appl. No.: 18/476,787

(22) Filed: Sep. 28, 2023

(65) Prior Publication Data

US 2024/0016460 A1      Jan. 18, 2024

Related U.S. Application Data

(63) Continuation of application No. PCT/JP2022/010572, filed on Mar. 10, 2022.

(30) Foreign Application Priority Data

Mar. 29, 2021    (JP) ................................. 2021-055867

(51) Int. Cl.
  *A61B 6/00*          (2024.01)
  *A61B 5/00*          (2006.01)
  *A61B 8/12*          (2006.01)
(52) U.S. Cl.
  CPC ............ *A61B 6/481* (2013.01); *A61B 5/0035* (2013.01); *A61B 5/0095* (2013.01); *A61B 8/12* (2013.01)
(58) Field of Classification Search
  None
  See application file for complete search history.

(56) References Cited

U.S. PATENT DOCUMENTS

2005/0101859 A1    5/2005  Maschke
2008/0177183 A1*   7/2008  Courtney ........... A61B 1/00172
                                              600/463

(Continued)

FOREIGN PATENT DOCUMENTS

JP        2005095624  A      4/2005
JP        2017506933  A      3/2017

(Continued)

OTHER PUBLICATIONS

Frimerman et al., "Novel Method for Real Time Co-Registration of IVUS and Coronary Angiography,"(Apr. 8, 2016), Journal of Interventional Cardiology, 29: 225-231. (Year: 2016).*

(Continued)

*Primary Examiner* — Keith M Raymond
*Assistant Examiner* — Ashish S. Jasani
(74) *Attorney, Agent, or Firm* — Buchanan Ingersoll & Rooney PC

(57) ABSTRACT

A non-transitory computer-readable medium storing a computer program capable of providing an easy-to-interpret image. A computer acquires, according to a computer program, a signal data set by a first inspection wave emitted in a direction inclined at a first angle with respect to a longitudinal axis direction of an imaging core used in a catheter. Then, the computer constructs an image obtained by using a direction inclined at a second angle different from the first angle with respect to the longitudinal axis direction of the imaging core as an observation target, based on the acquired signal data set.

20 Claims, 22 Drawing Sheets

(56)　　　　References Cited

U.S. PATENT DOCUMENTS

| | | | |
|---|---|---|---|
| 2014/0176961 A1* | 6/2014 | Johansson | G01B 21/045 |
| | | | 356/479 |
| 2015/0005626 A1 | 1/2015 | Kaneko | |
| 2015/0057958 A1* | 2/2015 | Watanabe | G01B 9/02004 |
| | | | 702/94 |
| 2015/0196285 A1* | 7/2015 | Mori | A61B 8/58 |
| | | | 600/427 |
| 2015/0209526 A1 | 7/2015 | Matsubara et al. | |
| 2017/0181728 A1 | 6/2017 | Tokida | |
| 2019/0099079 A1* | 4/2019 | Yamada | A61B 5/0071 |

FOREIGN PATENT DOCUMENTS

| | | |
|---|---|---|
| WO | 2013145689 A1 | 10/2013 |
| WO | 2016047772 A1 | 3/2016 |

OTHER PUBLICATIONS

Zhang et al., "Simultaneous Registration of Location and Orientation in Intravascular Ultrasound Pullbacks Pairs Via 3D Graph-Based Optimization," (Jun. 11, 2015), IEEE Transactions on Medical Imaging, vol. 34, Issue: 12, Dec. 2015. (Year: 2015).*

Molony et al., "Evaluation of a framework for the co-registration of intravascular ultrasound and optical coherence tomography coronary artery pullbacks," (Dec. 2016), Journal of Biomechanics, vol. 49, Issue 16, Dec. 8, 2016, pp. 4048-4056. (Year: 2016).*

Van der Sijde et al., "The OPTIS Integrated System: real-time, co-registration of angiography and optical coherence tomography," (Sep. 18, 2016), EuroIntervention 2016;12:855-860. (Year: 2016).*

Carlier et al., "A new method for real-time co-registration of 3D coronary angiography and intravascular ultrasound or optical coherence tomography," (Jun. 2014) Cardiovasc Revasc Med, Jun. 2014;15(4):226-32. (Year: 2015).*

International Search Report (PCT/ISA/210) with translation and Written Opinion (PCT/ISA/237) mailed on May 17, 2022, by the Japan Patent Office as the International Searching Authority for International Application No. PCT/JP2022/010572. (8 pages).

English Translations of the International Search Report (Form PCT/ISA/210) and the Written Opinion of the International Searching Authority (Form PCT/ISA/237) issued May 17, 2022, by the Japan Patent Office in corresponding International Application No. PCT/JP2022/010572. (6 pages).

* cited by examiner

*FIG. 1*

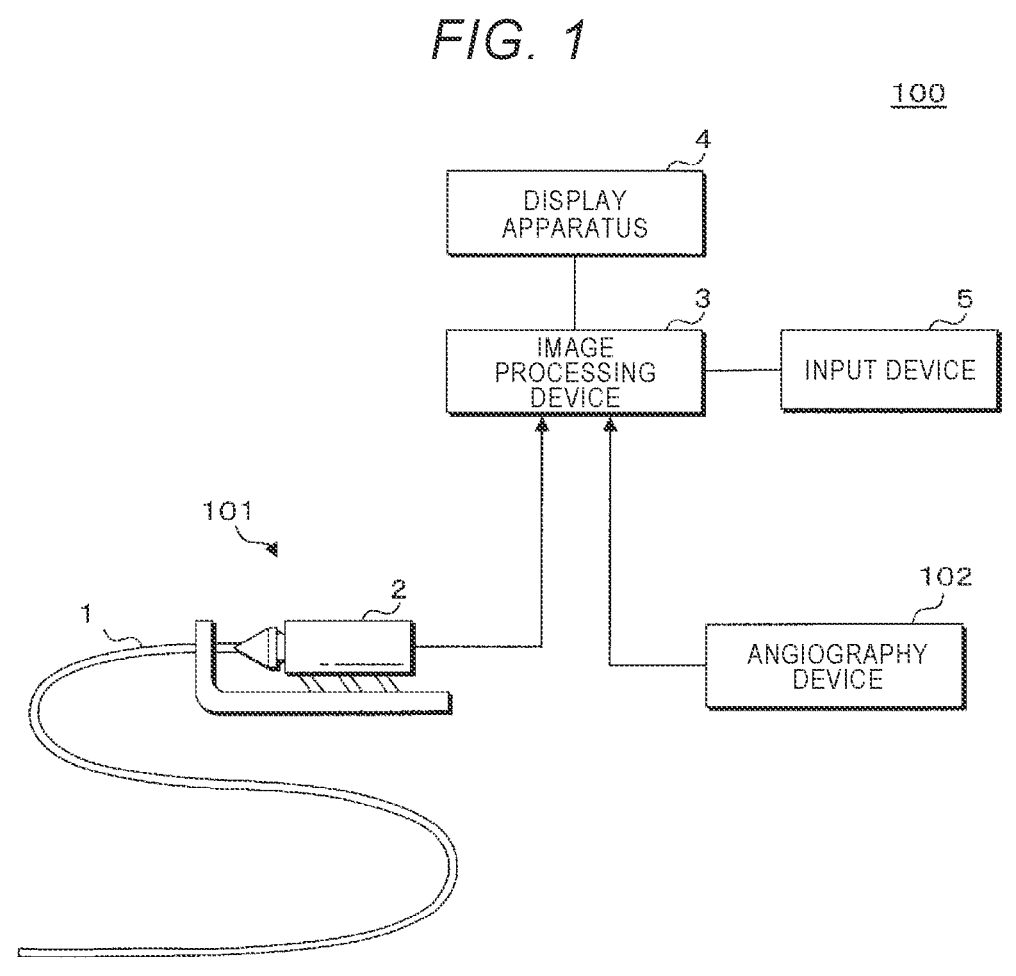

TOMOGRAPHIC IMAGE
(IVUS IMAGE, OCT IMAGE)

DISTAL END SIDE

TIME

PROXIMAL END
SIDE

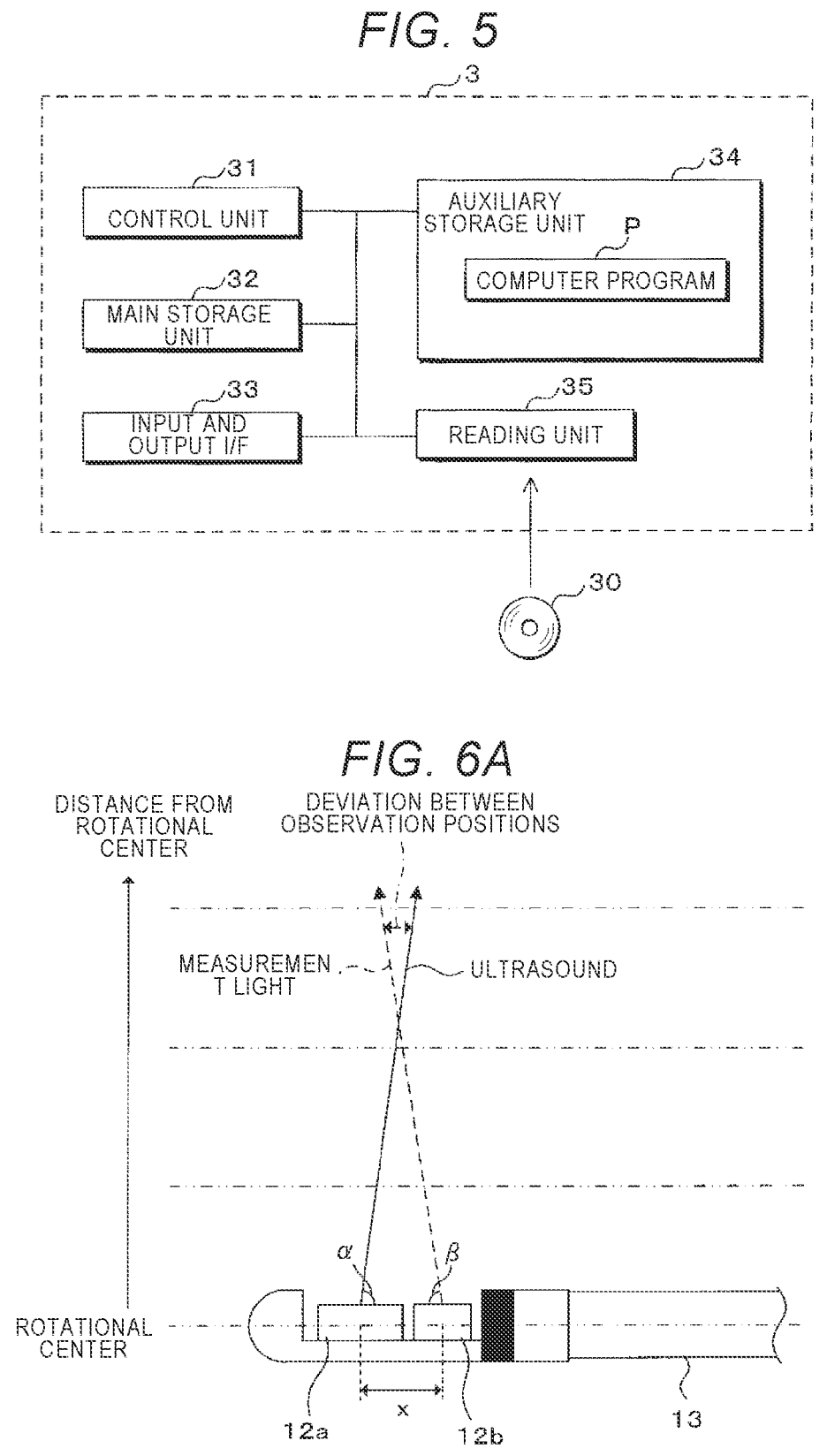

┌─────────────────────────────────────────────────────────────┐
│                                                               │
│   ┌──────────────┐ 31      ┌─────────────────────┐ 34        │
│   │              │         │  AUXILIARY          │           │
│   │ CONTROL UNIT │         │  STORAGE UNIT    P  │           │
│   │              │         │   ┌───────────────────┐         │
│   └──────────────┘         │   │ COMPUTER PROGRAM  │         │
│                            │   └───────────────────┘         │
│   ┌──────────────┐ 32      │                     │           │
│   │ MAIN STORAGE │         │                     │           │
│   │    UNIT      │         └─────────────────────┘           │
│   └──────────────┘                                           │
│                                                               │
│   ┌──────────────┐ 33      ┌─────────────────────┐ 35        │
│   │ INPUT AND    │         │   READING UNIT      │           │
│   │ OUTPUT I/F   │         │                     │           │
│   └──────────────┘         └─────────────────────┘           │
│                                                               │
└─────────────────────────────────────────────────────────────┘
                                            ▲
                                            │
                                          ◎  30
```

FIG. 6A

DISTANCE FROM
ROTATIONAL
CENTER

DEVIATION BETWEEN
OBSERVATION POSITIONS

MEASUREMEN
T LIGHT          ULTRASOUND $\alpha$          $\beta$

ROTATIONAL
CENTER 12a          x          12b          13

FIG. 10

| DEVIATION AMOUNT BETWEEN OBSERVATION POSITIONS Δx [mm] | CORRECTION FRAME NUMBER | DISTANCE FROM ROTATIONAL CENTER L [mm] |
|---|---|---|
| 0.1 | 1 | 3.64 |
| 0.2 | 2 | 3.12 |
| 0.3 | 3 | 2.60 |
| 0.4 | 4 | 2.08 |
| 0.5 | 5 | 1.56 |
| 0.6 | 6 | 1.04 |
| 0.7 | 7 | 0.52 |

FIG. 12

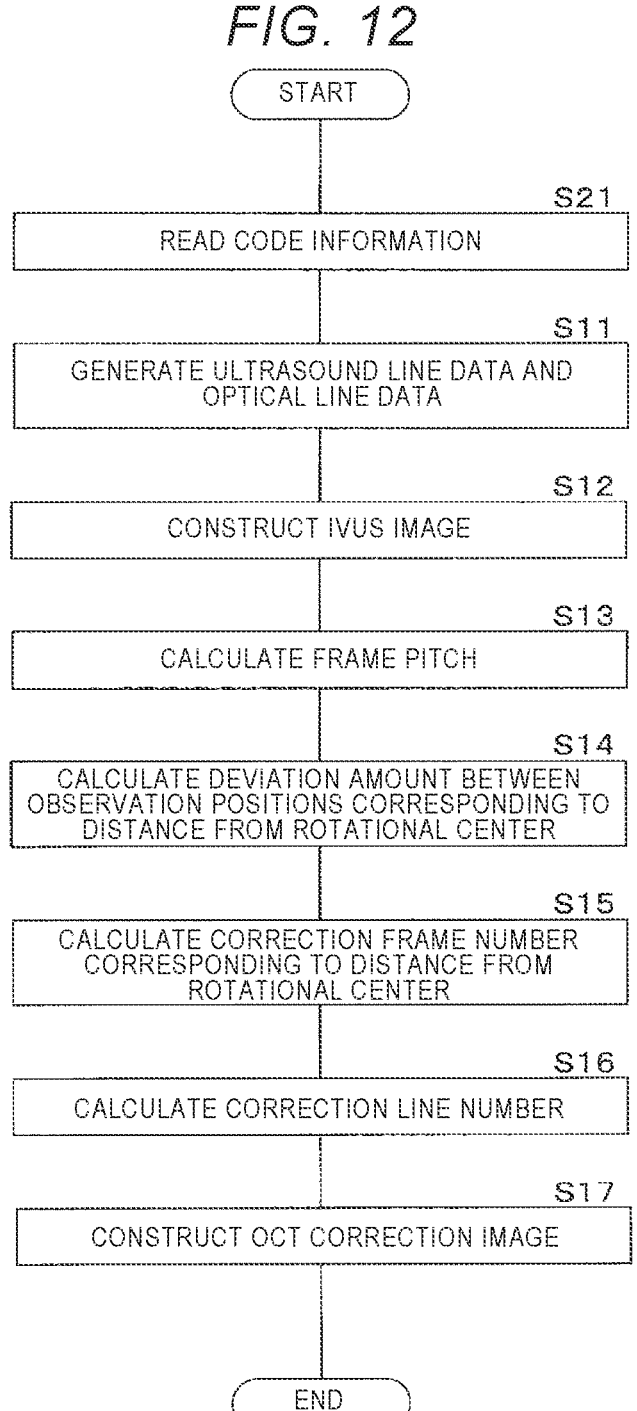

START

S21
READ CODE INFORMATION

S11
GENERATE ULTRASOUND LINE DATA AND
OPTICAL LINE DATA

S12
CONSTRUCT IVUS IMAGE

S13
CALCULATE FRAME PITCH

S14
CALCULATE DEVIATION AMOUNT BETWEEN
OBSERVATION POSITIONS CORRESPONDING TO
DISTANCE FROM ROTATIONAL CENTER

S15
CALCULATE CORRECTION FRAME NUMBER
CORRESPONDING TO DISTANCE FROM
ROTATIONAL CENTER

S16
CALCULATE CORRECTION LINE NUMBER

S17
CONSTRUCT OCT CORRECTION IMAGE

END

| SERIAL NUMBER | DISTANCE BETWEEN SENSORS x [mm] | ANGLE OF ULTRASOUND α [°] | ANGLE OF MEASUREMENT LIGHT β [°] | DEVIATION IN CIRCUMFERENTIAL DIRECTION φ [°] |
|---|---|---|---|---|
| 1111 | 0.80 | 86 | 85 | 10 |
| 2222 | 0.60 | 86 | 79 | 15 |
| 3333 | 0.70 | 85 | 86 | 20 |
| ... | ... | ... | ... | ... |

FIG. 21

ANGULAR DEVIATION CALIBRATION OF IVUS AND OCT DURING ENDOSCOPY

CROSS-REFERENCES TO RELATED APPLICATIONS

This application is a continuation of International Application No. PCT/JP2022/010572 filed on Mar. 10, 2022, which claims priority to Japanese Patent Application No. 2021-055867 filed on Mar. 29, 2021, the entire content of both of which is incorporated herein by reference.

TECHNOLOGICAL FIELD

The present disclosure generally relates to a program, an image processing method, and an image processing device.

BACKGROUND DISCUSSION

As a minimally invasive treatment for angina pectoris, myocardial infarction, or the like, an intravascular treatment represented by percutaneous coronary intervention (PCI) is performed. PCI is a therapeutic method in which a catheter is inserted into a blood vessel from a wrist, an elbow, or a groin, and a balloon or a stent is used to dilate a stenosis area of a coronary artery. The catheter is provided with, for example, an intravascular ultrasound (IVUS) examination sensor, and an operator can confirm the stenosis area in the blood vessel by an IVUS image obtained by imaging the inside of the blood vessel with the IVUS sensor. Examples of the catheter include a catheter provided with an optical coherence tomography (OCT) sensor using near-infrared light. Japanese Patent Application Publication No. 2005-95624A discloses a catheter provided with an IVUS sensor and an OCT sensor.

In the catheter disclosed in Japanese Patent Application Publication No. 2005-95624 A, the IVUS sensor and the OCT sensor are provided at different positions in a longitudinal axis direction of the catheter (running direction of a blood vessel). Therefore, a deviation occurs between an observation position of the IVUS sensor and an observation position of the OCT sensor at the same imaging timing. Therefore, interpretation of an IVUS image and an OCT image can be complicated, and accuracy of a procedure performed while confirming the IVUS image and the OCT image may decrease.

In addition, a contrast marker formed of an X-ray opaque material is provided on the catheter, and a position of the catheter is confirmed by the contrast marker captured in an X-ray image, and the stenosis area is confirmed at the same time by the IVUS image and the OCT image. Also in such a configuration, the IVUS sensor or OCT sensor and the contrast marker are provided at different positions in the longitudinal axis direction of the catheter, and a deviation can occur between a position of the contrast marker in the X-ray image and the observation position of the IVUS sensor or OCT sensor at the same imaging timing. Therefore, also in such a configuration, the interpretation of the IVUS image or OCT image can be complicated.

SUMMARY

A non-transitory computer-readable medium storing a program when executed by a computer performs a process that provides an easy-to-interpret image based on an image captured using a catheter.

A non-transitory computer-readable medium storing a program according to one aspect causes a computer to execute a process of: acquiring a signal data set by a first inspection wave emitted in a direction inclined at a first angle with respect to a longitudinal axis direction of an imaging core used in a catheter; and constructing an image obtained by using a direction inclined at a second angle different from the first angle with respect to the longitudinal axis direction as an observation target, based on the acquired signal data set.

An image processing method executed by a computer, the method comprising: acquiring a signal data set by a first inspection wave emitted in a direction inclined at a first angle with respect to a longitudinal axis direction of an imaging core of a catheter; and constructing an image obtained by using a direction inclined at a second angle different from the first angle with respect to the longitudinal axis direction as an observation target, based on the acquired signal data set.

An image processing device comprising: a control unit configured to: acquire a signal data set by a first inspection wave emitted in a direction inclined at a first angle with respect to a longitudinal axis direction of an imaging core of a catheter; and construct an image obtained by using a direction inclined at a second angle different from the first angle with respect to the longitudinal axis direction as an observation target, based on the acquired signal data set.

According to one aspect, an image that is rather easy for an operator to interpret can be provided based on an image captured using the catheter.

BRIEF DESCRIPTION OF THE DRAWINGS

FIG. 1 is a diagram illustrating a configuration example of an image diagnosis apparatus.

FIG. 5 is a block diagram showing a configuration example of an image processing device.

FIG. 6A is a diagram illustrating a deviation between observation positions of an IVUS sensor and an OCT sensor.

FIG. 10 is a diagram illustrating an example of calculation results of correction frame numbers corresponding to distances.

FIG. 12 is a flowchart showing an example of a tomographic image correction processing procedure in Embodiment 2.

FIG. 14 is a schematic diagram showing a configuration example of a catheter database (DB).

FIG. 21 is a diagram illustrating the processing of correcting the deviation of the observation position.

DETAILED DESCRIPTION

Figure 2:
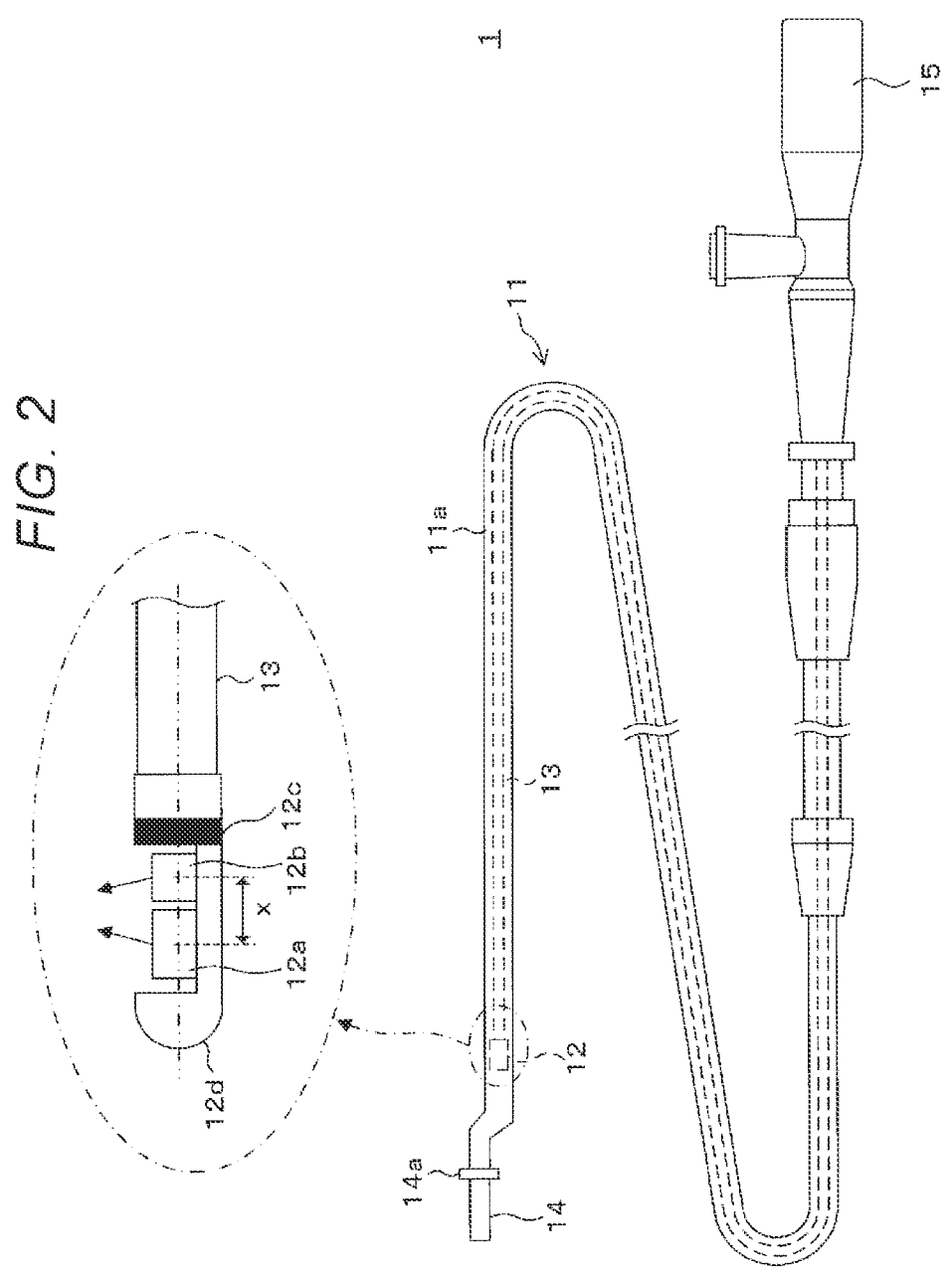
FIG. 2 is a diagram illustrating an outline of an image diagnosis catheter.

Set forth below with reference to the accompanying drawings is a detailed description of embodiments of a program, an image processing method, and an image processing device. In each of the following embodiments, a cardiac catheter treatment, which is an intravascular treatment, will be described as an example. However, a luminal organ targeted for the catheter treatment is not limited to a blood vessel, and may be other luminal organs such as a bile duct, a pancreatic duct, bronchi, and an intestine.

Embodiment 1

FIG. 1 is a diagram illustrating a configuration example of an image diagnosis apparatus 100. In the present embodiment, an image diagnosis apparatus using a dual-type catheter having both functions of an intravascular ultrasound diagnosis method (IVUS) and an optical coherence tomography diagnosis method (OCT) will be described. The dual-type catheter has a mode for acquiring an ultrasound tomographic image only by the IVUS, a mode for acquiring an optical coherence tomographic image only by the OCT, and a mode for acquiring both tomographic images by the IVUS and OCT, and these modes can be switched and used. Hereinafter, the ultrasound tomographic image and the optical coherence tomographic image will be referred to as an IVUS image and an OCT image, respectively. In addition, the IVUS image and the OCT image are collectively referred to as tomographic images.

The image diagnosis apparatus 100 of the present embodiment includes an intravascular examination device 101, an angiography device 102, an image processing device 3, a display apparatus 4, and an input device 5. The intravascular examination device 101 includes an image diagnosis catheter 1 and a motor drive unit (MDU) 2. The image diagnosis catheter 1 is connected to the image processing device 3 via the MDU 2. The display apparatus 4 and the input device 5 are connected to the image processing device 3. The display apparatus 4 is, for example, a liquid crystal display or an organic electro-luminence (EL) display, and the input device 5 can be, for example, a keyboard, a mouse, a trackball, or a microphone. The display apparatus 4 and the input device 5 may be stacked integrally (i.e., combined into one) to form a touch panel. In addition, the input device 5 and the image processing device 3 may be integrated. Furthermore, the input device 5 may be a sensor that receives gesture input, line-of-sight input, or the like.

The angiography device 102 is connected to the image processing device 3. The angiography device 102 can be an angiography device that images a blood vessel using X-rays from outside a living body of a patient while injecting a contrast agent into the blood vessel of the patient to obtain an angiographic image, which is a fluoroscopic image of the blood vessel. The angiography device 102 can include an X-ray source and an X-ray sensor, and the X-ray sensor receives X-rays emitted from the X-ray source to capture an X-ray fluoroscopic image (X-ray image) of the patient. The image diagnosis catheter 1 is provided with a marker formed of an X-ray opaque material that does not transmit the X-rays, and a position of the image diagnosis catheter 1 (marker) can be visualized in the angiographic image. The angiography device 102 outputs the angiographic image obtained by imaging to the image processing device 3 and the angiographic image is displayed on the display apparatus 4 via the image processing device 3. The display apparatus 4 displays the angiographic image and a tomographic image captured using the image diagnosis catheter 1.

FIG. 2 is a diagram illustrating an outline of the image diagnosis catheter 1. An upper one-dot chain line area in FIG. 2 is an enlarged view of a lower one-dot chain line area. The image diagnosis catheter 1 can include a probe 11 and a connector portion 15 disposed at an end of the probe 11. The probe 11 is connected to the MDU 2 via the connector portion 15. In the following descriptions, a side far from the connector portion 15 of the image diagnosis catheter 1 is referred to as a distal end side, and a connector portion 15 side is referred to as a proximal end side. The probe 11 can include a catheter sheath 11a, and a guide wire insertion portion 14 through which a guide wire can be inserted is provided at a distal end of the probe 11. The guide wire insertion portion 14 constitutes a guide wire lumen, and is used to receive a guide wire previously inserted into the blood vessel and guide the probe 11 to an affected area by the guide wire. The catheter sheath 11a constitutes a tube portion that is continuous from a connection portion with the guide wire insertion portion 14 to a connection portion with the connector portion 15. A shaft 13 is inserted through the inside of the catheter sheath 11a, and a sensor portion 12 is connected to a distal end side of the shaft 13.

The sensor portion 12 includes a housing 12d, and a distal end side of the housing 12d is formed in a hemispherical shape to reduce friction and catching with an inner surface of the catheter sheath 11a. An ultrasound transmitter and receiver 12a (hereinafter referred to as an IVUS sensor 12a) that transmits ultrasound into the blood vessel and receives a reflected wave from the blood vessel, and an optical transmitter and receiver 12b (hereinafter referred to as an OCT sensor 12b) that transmits near-infrared light into the blood vessel and receives a reflected light from the blood vessel are disposed in the housing 12d. In the example shown in FIG. 2, the IVUS sensor 12a is provided on a distal end side of the probe 11, the OCT sensor 12b is provided on a proximal end side of the probe 11, and the IVUS sensor 12a and the OCT sensor 12b are disposed by a distance x along an axial direction (longitudinal axis direction of the shaft 13) on a central axis of the shaft 13 (on the chain double-dashed line in FIG. 2). In the image diagnosis catheter 1, the IVUS sensor 12a and the OCT sensor 12b are attached using a direction of approximately 90 degrees with respect to the axial direction of the shaft 13 (radial direction of shaft 13) as a transmission and reception direction of the ultrasound or the near-infrared light. It is desirable that the IVUS sensor 12a and the OCT sensor 12b are attached with a slight deviation from the radial direction so as not to receive a reflected wave or a reflected light from the inner surface of the catheter sheath 11a. In the present embodiment, for example, as indicated by arrows in FIG. 2, the IVUS sensor 12a is attached using a direction inclined toward the proximal end side with respect to the radial direction as an emitting direction of the ultrasound, and the OCT sensor 12b is attached using a direction inclined toward the distal end side with respect to the radial direction as an emitting direction of the near-infrared light.

An electric signal cable connected to the IVUS sensor 12a and an optical fiber cable connected to the OCT sensor 12b are inserted into the shaft 13. The probe 11 is inserted into the blood vessel from the distal end side. The sensor portion 12 and the shaft 13 can move forward and backward inside the catheter sheath 11a, and can rotate in a circumferential direction. The sensor portion 12 and the shaft 13 rotate about the central axis of the shaft 13 as a rotation axis. In the image diagnosis apparatus 100, by using an imaging core constituted by the sensor portion 12 and the shaft 13, a condition inside the blood vessel can be measured using an ultrasound tomographic image (IVUS image) obtained by imaging from the inside of the blood vessel or an optical coherence tomographic image (OCT image) obtained by imaging from the inside of the blood vessel.

The MDU 2 is a driving device to which the probe 11 (image diagnosis catheter 1) is detachably attached by the connector portion 15, and controls operations of the image diagnosis catheter 1 inserted into the blood vessel by driving a built-in motor according to operations of a health-care professional. For example, the MDU 2 performs a pullback operation in which the sensor portion 12 and shaft 13 inserted into the probe 11 are pulled toward the MDU 2 at a constant speed and rotated in the circumferential direction. The sensor portion 12 continuously scans the inside of the blood vessel at a predetermined time interval while rotating and moving from the distal end side to the proximal end side by the pullback operation, thereby continuously capturing a plurality of transverse layer images substantially perpendicular to the probe 11 at a predetermined interval. The MDU 2 outputs reflected wave data of ultrasound received by the IVUS sensor 12a and reflected light data received by the OCT sensor 12b to the image processing device 3.

Figure 3:
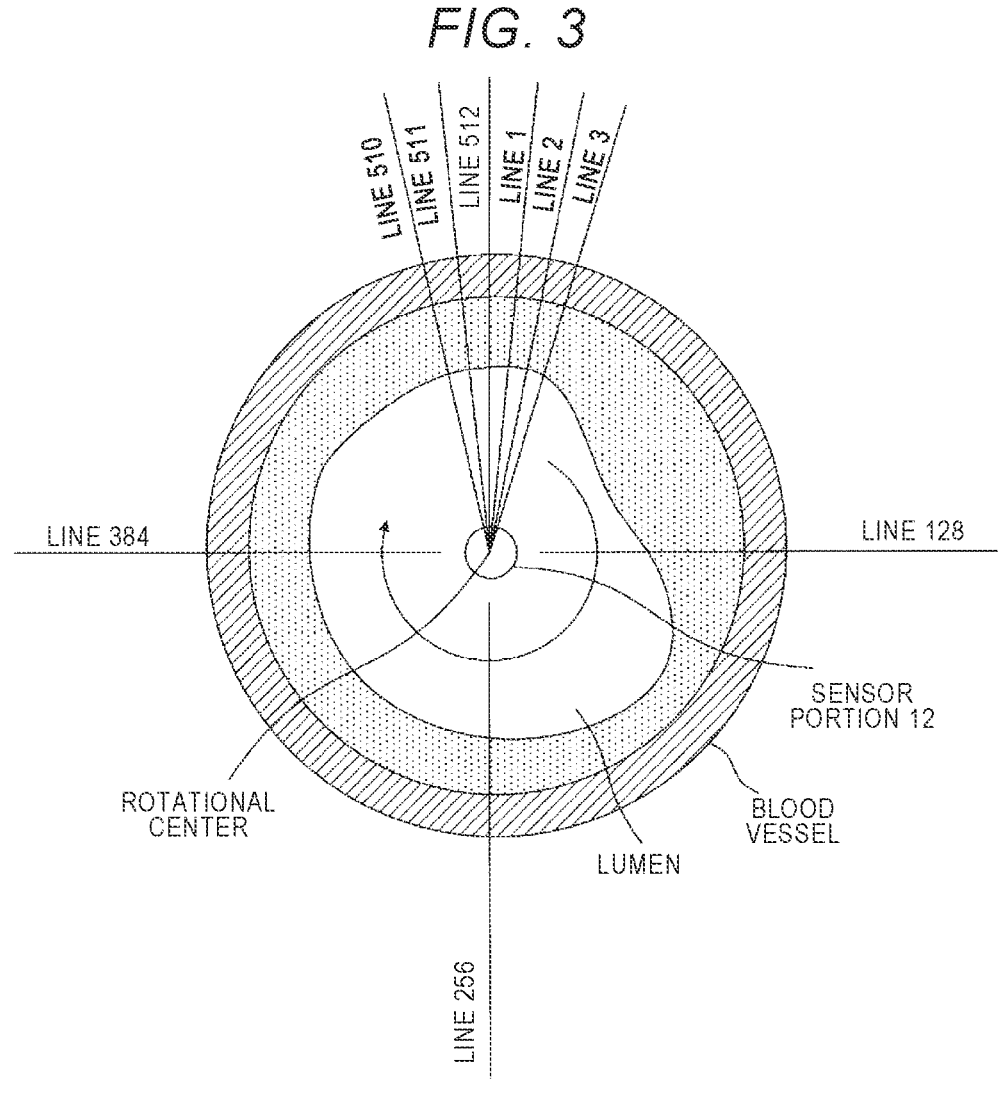
FIG. 3 is a diagram illustrating a cross section of a blood vessel through which a sensor portion is inserted.
Figure 4A:
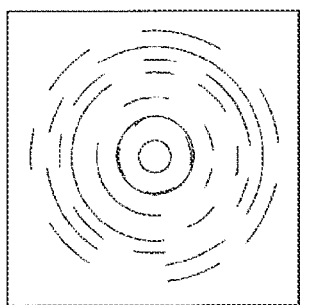
FIG. 4A is a diagram illustrating a tomographic image.
Figure 4B:
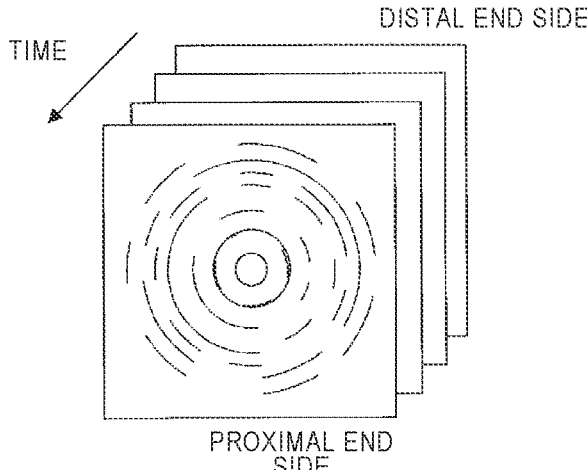
FIG. 4B is a diagram illustrating the tomographic image.

The image processing device 3 acquires the reflected wave data of ultrasound received by the IVUS sensor 12a and the reflected light data received by the OCT sensor 12b, via the MDU 2. The image processing device 3 generates ultrasound line data, which is a signal data set, from the reflected wave data of ultrasound, and constructs an ultrasound tomographic image (IVUS image) obtained by imaging a transverse layer of the blood vessel based on the generated ultrasound line data. The image processing device 3 also generates optical line data, which is a signal data set, from the reflected light data, and constructs an optical tomographic image (OCT image) obtained by imaging a transverse layer of the blood vessel based on the generated optical line data. Here, signal data sets acquired by the IVUS sensor 12a and the OCT sensor 12b and tomographic images constructed based on the signal data sets will be described. FIG. 3 is a diagram illustrating a cross section of a blood vessel through which the sensor portion 12 is inserted, and FIGS. 4A and 4B are diagrams illustrating tomographic images.

First, operations of the IVUS sensor 12a and the OCT sensor 12b in the blood vessel and the signal data sets (ultrasound line data and optical line data) acquired by the IVUS sensor 12a and the OCT sensor 12b will be described with reference to FIG. 3. When imaging of the tomographic images is started under a state where the sensor portion 12 and the shaft 13 are inserted into the blood vessel, the sensor portion 12 rotates about the central axis of the shaft 13 as a rotational center in a direction indicated by an arrow. At this time, the IVUS sensor 12a transmits and receives the ultrasound at each rotation angle. Lines 1, 2, . . . , 512 indicate ultrasound transmission and reception directions at these rotation angles. In the present embodiment, the IVUS sensor 12a intermittently transmits and receives the ultrasound 512 times while rotating 360 degrees (one rotation) in the blood vessel. The IVUS sensor 12a acquires data of one line (signal data) on the transmission and reception direction by transmitting and receiving the ultrasound one time. Therefore, ultrasound line data of 512 lines radially extending from the rotational center can be obtained during one rotation. The ultrasound line data of the 512 lines are dense near the rotational center, and become sparse with each other as a distance from the rotational center increases. Therefore, the image processing device 3 can construct a two-dimensional ultrasound tomographic image (IVUS image) as shown in FIG. 4A by generating pixels in empty spaces in each line by interpolation processing.

Similarly, the OCT sensor 12b also transmits and receives the near-infrared light (measurement light) at each rotation angle. The OCT sensor 12b also transmits and receives the measurement light 512 times while rotating 360 degrees in the blood vessel. Therefore, optical line data of 512 lines radially extending from the rotational center can be obtained during one rotation. Regarding the optical line data, the image processing device 3 also can construct a two-dimensional optical coherence tomographic image (OCT image) similar to the IVUS image shown in FIG. 4A by generating pixels in empty spaces in each line by interpolation processing.

The two-dimensional tomographic image constructed based on the line data of 512 lines in this way is called an IVUS image or OCT image of one frame. Since the sensor portion 12 scans the blood vessel while moving inside the blood vessel, the IVUS image or OCT image of one frame is acquired at each position at which the one rotation is performed within a movement range. That is, the IVUS image or OCT image of one frame is acquired at each position from the distal end side to the proximal end side of the probe 11 in the movement range. Therefore, as shown in FIG. 4B, IVUS images or OCT images of a plurality of frames are acquired in the movement range. In the present embodiment, each of the IVUS sensor 12a and the OCT sensor 12b has a configuration that acquires the line data of 512 lines, but the number of line data to be acquired by the IVUS sensor 12a and the OCT sensor 12b is not limited to 512.

The image diagnosis catheter 1 can include markers that do not transmit X-rays to confirm a positional relationship between the IVUS image obtained by the IVUS sensor 12a or the OCT image obtained by the OCT sensor 12b and the angiographic image obtained by the angiography device 102. In the example shown in FIG. 2, a marker 14a is provided at the distal end portion of the catheter sheath 11a, for example, at the guide wire insertion portion 14, and a marker 12*c* is provided at the sensor portion 12 on the shaft 13 side. When the image diagnosis catheter 1 configured in this way is imaged with X-rays, an angiographic image in which the markers 14*a* and 12*c* are visualized can be obtained. The positions at which the markers 14*a* and 12*c* are provided are examples, the marker 12*c* may be provided on the shaft 13 instead of the sensor portion 12, and the marker 14*a* may be provided at a location other than the distal end of the catheter sheath 11*a*.

FIG. 5 is a block diagram showing a configuration example of the image processing device 3. The image processing device 3 is a computer and can include a control unit 31, a main storage unit 32, an input and output I/F 33, an auxiliary storage unit 34, and a reading unit 35. The control unit 31 can include one or a plurality of computational processing units such as a central processing unit (CPU), a micro-processing unit (MPU), a graphics processing unit (GPU), a general-purpose computing on graphics processing unit (GPGPU), and a tensor processing unit (TPU). The control unit 31 is connected to each hardware unit constituting the image processing device 3 via a bus.

The main storage unit 32 is a temporary storage area of a static random access memory (SRAM), a dynamic random access memory (DRAM), a flash memory, or the like, and temporarily stores data required for the control unit 31 to execute computational processing.

The input and output I/F 33 is an interface to which the intravascular examination device 101, the angiography device 102, the display apparatus 4, and the input device 5 are connected. The control unit 31 acquires the reflected wave data of ultrasound and the reflected light data of measurement light from the intravascular examination device 101 and acquires the angiographic image from the angiography device 102 via the input and output I/F 33. The control unit 31 generates the ultrasound line data from the reflected wave data acquired from the intravascular examination device 101, and further constructs the IVUS image. The control unit 31 generates the optical line data from the reflected light data acquired from the intravascular examination device 101, and further constructs the OCT image. In addition, the control unit 31 displays a medical image on the display apparatus 4 by outputting a medical image signal of the IVUS image, the OCT image, or the angiographic image to the display apparatus 4 via the input and output I/F 33. Furthermore, the control unit 31 receives information input to the input device 5 via the input and output I/F 33.

The auxiliary storage unit 34 is a storage device such as a hard disk, an electrically erasable programmable ROM (EEPROM), or a flash memory. The auxiliary storage unit 34 stores a computer program P executed by the control unit 31 and various types of data required for processing of the control unit 31. The auxiliary storage unit 34 may be an external storage device connected to the image processing device 3. The computer program P may be written in the auxiliary storage unit 34 at a stage of manufacturing the image processing device 3, or the image processing device 3 may acquire a program distributed by a remote server device through communication and store the program in the auxiliary storage unit 34. The computer program P may be in a state of being recorded readably in a recording medium 30 such as a magnetic disk, an optical disk, or a semiconductor memory, or may be read from the recording medium 30 by the reading unit 35 and stored in the auxiliary storage unit 34.

The image processing device 3 may be a multi-computer including a plurality of computers. In addition, the image processing device 3 may be a server client system, a cloud server, or a virtual machine virtually constructed by software. In the following descriptions, the image processing device 3 will be described as one computer. In the present embodiment, the image processing device 3 is connected to the angiography device 102 that captures two-dimensional angiographic images, and such a device is not limited to the angiography device 102 as long as it is a device that images lumenal organs of a patient and the image diagnosis catheter 1 from a plurality of directions outside a living body.

In the image processing device 3 of the present embodiment, the control unit 31 reads and executes the computer program P stored in the auxiliary storage unit 34, thereby generating the ultrasound line data from the reflected wave data received by the IVUS sensor 12*a* and generating the optical line data from the reflected light data received by the OCT sensor 12*b*. Furthermore, the control unit 31 performs the processing of constructing the IVUS image based on the ultrasound line data, and performs the processing of constructing the OCT image based on the optical line data. As will be described later, a deviation occurs between the observation positions of the IVUS sensor 12*a* and the OCT sensor 12*b* at the same imaging timing. Therefore, the control unit 31 performs processing of correcting the deviation between the observation positions in the IVUS image and the OCT image when constructing the IVUS image and the OCT image. Therefore, the image processing device 3 of the present embodiment can construct an IVUS image and an OCT image in which the observation positions are matched, and can provide a relatively easy-to-interpret image.

Figure 6B:
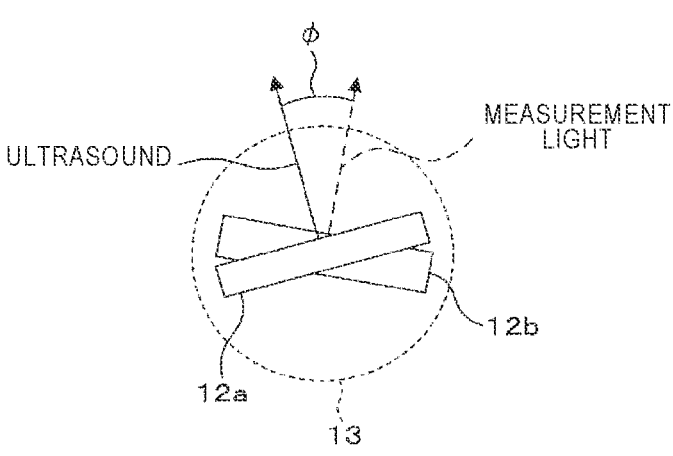
FIG. 6B is a diagram illustrating the deviation between the observation positions of the IVUS sensor and the OCT sensor.

FIGS. 6A and 6B are diagrams illustrating the deviation between the observation positions of the IVUS sensor 12*a* and the OCT sensor 12*b*. FIG. 6A shows a state where the sensor portion 12 is viewed from the radial direction of the shaft 13, and FIG. 6B shows a state where the sensor portion 12 is viewed from the distal end side of the probe 11. In FIGS. 6A and 6B, a solid line arrow indicates an ultrasound transmission and reception direction of the IVUS sensor 12*a*, and a broken line arrow indicates a measurement light transmission and reception direction of the OCT sensor 12*b*.

In the sensor portion 12 of the present embodiment, the IVUS sensor 12*a* uses a direction inclined toward the proximal end side with respect to the radial direction of the shaft 13 as the ultrasound transmission and reception direction, and in the example shown in FIG. 6A, the ultrasound transmission and reception direction defines an angle α with respect to a direction of the proximal end side on the central axis of the shaft 13. In addition, the OCT sensor 12*b* uses a direction inclined toward the distal end side with respect to the radial direction of the shaft 13 as the measurement light transmission and reception direction, and the measurement light transmission and reception direction defines an angle β with respect to a direction of the distal end side on the central axis of the shaft 13. In the IVUS sensor 12*a* and the OCT sensor 12*b*, as shown in FIG. 6A, a path of the ultrasound and a path of the measurement light intersect, and the same object is observed at the intersection position, but at other locations, such that deviations in the axial direction of the shaft 13 occur between the observation positions of the IVUS sensor 12*a* and the OCT sensor 12*b*. A smallest deviation between the observation positions occurs at the intersection position of the ultrasound and the measurement light, and the deviations increase as a distance from the intersection position increases. In addition, in an area on the sensor portion 12 side relative to the intersection position, the observation by the OCT sensor 12*b* is performed prior to the observation by the IVUS sensor 12*a* (i.e., the OCT sensor 12b is located proximal to the IVUS sensor 12a relative to the shaft 13), and in an area farther than the intersection position, the observation by the IVUS sensor 12a is performed prior to the observation by the OCT sensor 12b. Therefore, observation orders are different. Such a deviation between the observation positions varies depending on the distance x between arrangement positions of the sensors 12a and 12b, attachment angles of the sensors 12a and 12b (the angle α of the ultrasound transmission and reception direction, the angle β of the measurement light transmission and reception direction), and a distance from the rotational center of the sensor portion 12 to the observation positions. The distance x between the arrangement positions of the sensors 12a and 12b and the attachment angles of the sensors 12a and 12b include an individual difference that occurs during a process for manufacturing the image diagnosis catheter 1. Therefore, a deviation amount between the observation positions at each distance from the rotational center of the sensor portion 12 to the observation positions differs for each image diagnosis catheter 1.

In addition, as shown in FIG. 6B, between the ultrasound transmission and reception direction of the IVUS sensor 12a and the measurement light transmission and reception direction of the OCT sensor 12b, deviations also occur in a rotation direction (circumferential direction) of the sensor portion 12. In the example shown in FIG. 6B, the measurement light transmission and reception direction is deviated by an angle φ with respect to the ultrasound transmission and reception direction, assuming that a clockwise direction is a positive direction. Therefore, the observation position of the IVUS sensor 12a and the observation position of the OCT sensor 12b are also deviated in the circumferential direction, and the deviation (angular difference) between the observation positions in the circumferential direction also varies depending on the attachment angles of the sensors 12a and 12b. Therefore, a deviation amount between the observation positions in the circumferential direction also differs for each image diagnosis catheter 1.

Figure 7A:
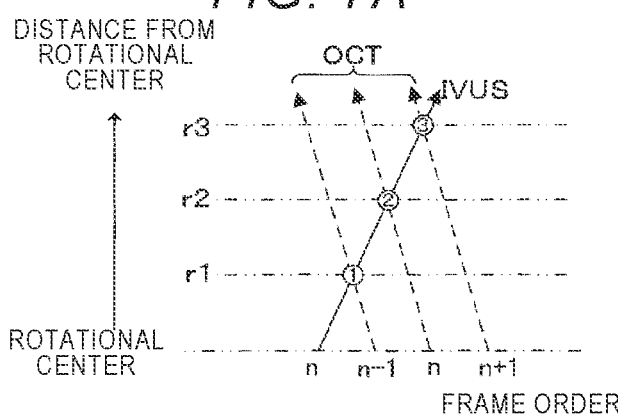
FIG. 7A is a diagram illustrating processing of correcting the deviation between the observation positions.
Figure 7B:
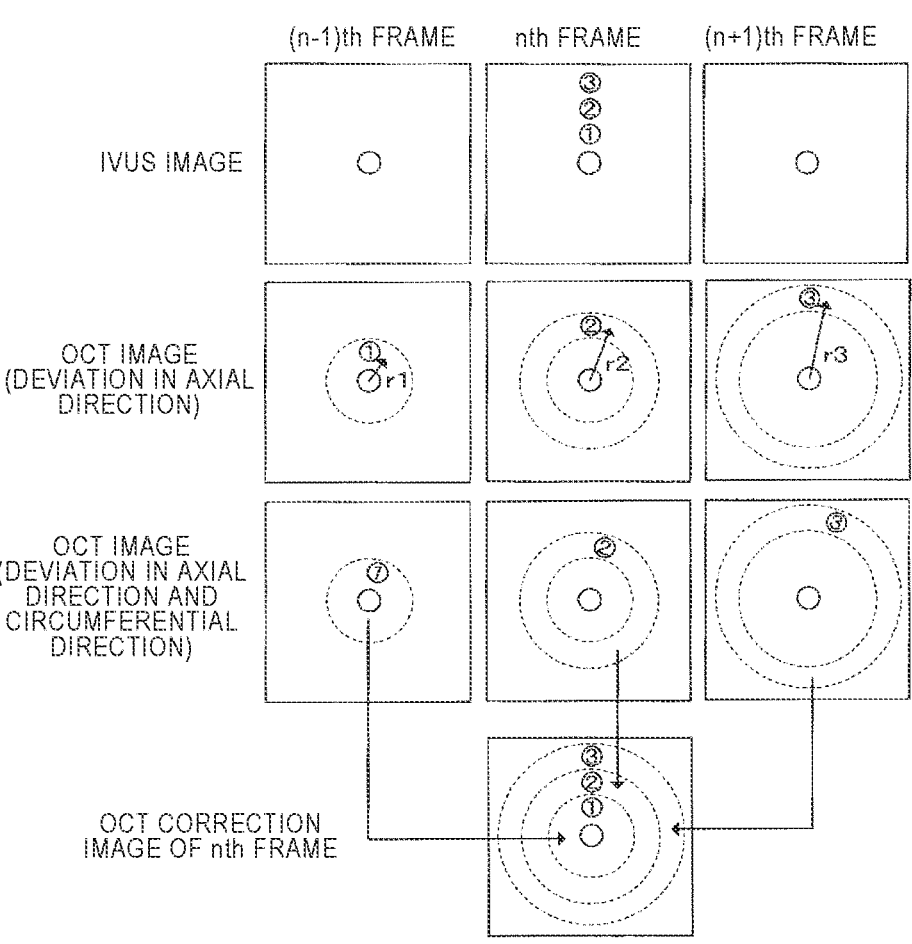
FIG. 7B is a diagram illustrating processing of correcting the deviation between the observation positions.

Therefore, when constructing the IVUS image and the OCT image based on the ultrasound line data and the optical line data, the image processing device 3 of the present embodiment constructs an IVUS image and an OCT image in which the deviation between the observation positions of the sensors 12a and 12b as described above is corrected. FIGS. 7A and 7B are diagrams illustrating processing of correcting the deviations between the observation positions. FIG. 7A is a diagram illustrating the deviation between the observation positions in the axial direction of the shaft 13, and FIG. 7B is a diagram illustrating processing of correcting the OCT images such that the observation positions in the OCT images and the observation positions in the IVUS images are matched, respectively.

FIG. 7A indicate observation positions at distances r1, r2, and r3 from the rotational center of the sensor portion 12. FIG. 7A shows that the OCT sensor 12b observes the observation position 1 in an (n−1)th frame, observes the observation position 2 in an nth frame, and observes the observation position 3 in an (n+1)th frame, and shows that the IVUS sensor 12a observes the observation positions 1 to 3 in the nth frame. In such a situation, as shown in an upper row in FIG. 7B, in the IVUS images, the observation positions 1 to 3 are imaged in the nth frame, and the observation positions 1 to 3 are not imaged in the (n−1)th frame or (n+1)th frame. On the other hand, as shown in a second row from the top in FIG. 7B, in the OCT images, the observation position 1 is imaged in the (n−1)th frame, the observation position 2 is imaged in the nth frame, and the observation position 3 is imaged in the (n+1)th frame. That is, in the example shown in FIG. 7A, an observation timing for the observation position 1 of the OCT sensor 12b is one frame before that of the IVUS sensor 12a, and an observation timing for the observation position 3 of the OCT sensor 12b is one frame after that of the IVUS sensor 12a. Therefore, the image processing device 3 can correct the IVUS images and the OCT images to a state where each observation position 1 to 3 is observed at the same observation timing (a state where each observation position 1 to 3 is imaged in a tomographic image having the same frame number), thereby correcting the deviation between the observation positions.

The deviation between the observation positions occurs not only in the axial direction of the shaft 13 but also in the circumferential direction (rotation direction) as shown in FIG. 6B. Therefore, as shown in a third row from the top in FIG. 7B, in the OCT images, the observation positions 1 to 3 are imaged at positions deviated by the angle φ in the circumferential direction, respectively. Therefore, as shown in a lower row in FIG. 7B, the image processing device 3 of the present embodiment performs correction processing of eliminating the deviation between the observation position of the OCT image and the observation position of the IVUS image by synthesizing each area in the OCT images of a plurality of frames to construct an OCT image of one frame. In the following description, processing of correcting the OCT image to match the observation target in the OCT image with the observation target in the IVUS image is performed, but processing of correcting the IVUS image in the same manner to match the observation target in the IVUS image with the observation target in the OCT image may be performed.

Figure 8:
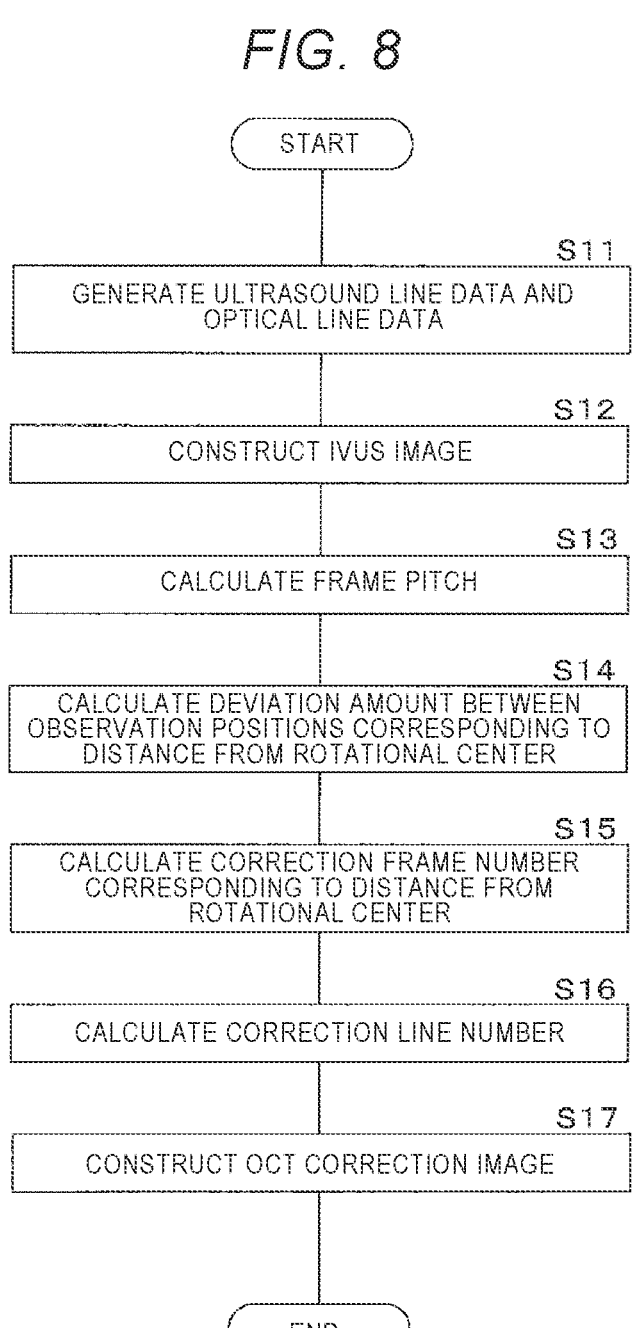
FIG. 8 is a flowchart showing an example of a tomographic image correction processing procedure.

FIG. 8 is a flowchart showing an example of a tomographic image correction processing procedure. The following processing is performed by the control unit 31 of the image processing device 3 according to the computer program P stored in the auxiliary storage unit 34. The distance x between the arrangement positions of the sensors 12a and 12b, the angle α (second angle) of the ultrasound transmission and reception direction of the IVUS sensor 12a, the angle β (first angle) of the measurement light transmission and reception direction of the OCT sensor 12b, which are shown in FIG. 6A, as well as the deviation amount in circumferential direction (angle φ) between the ultrasound transmission and reception direction and the measurement light transmission and reception direction shown in FIG. 6B are stored in the main storage unit 32 or the auxiliary storage unit 34. In the following description, correction processing of matching the observation target in the IVUS image generated based on the reflected wave data of ultrasound (second inspection wave) transmitted by the IVUS sensor 12a (second transmitter and receiver) with the observation target in the OCT image generated based on the reflected light data of measurement light (first inspection wave) transmitted by the OCT sensor 12b (first transmitter and receiver) is performed.

When the intravascular imaging processing is started by the intravascular examination device 101, the control unit 31 (acquisition unit) of the image processing device 3 acquires the reflected wave data of ultrasound from the IVUS sensor 12a via the MDU 2, and generates the ultrasound line data from the acquired reflected wave data of ultrasound. The control unit 31 also acquires the reflected light data from the OCT sensor 12b via the MDU 2, and generates the optical line data from the acquired reflected light data (S11). The control unit 31 constructs a two-dimensional IVUS image by interpolating the pixels by interpolation processing based on the ultrasound line data (S12). Then, the control unit 31 constructs an OCT image (hereinafter referred to as an OCT correction image) in which the observation target is matched with that in the IVUS image based on the optical line data. Specifically, first, the control unit 31 calculates a frame pitch at the time of imaging by the sensor portion 12 (S13). The frame pitch is a distance between frames of the tomographic images (distance between the observation positions in the frames in the axial direction of the shaft 13 (emitting interval of the measurement light)), and can be calculated based on a movement speed and a rotation speed of the sensor portion 12 during imaging. Specifically, the frame pitch is calculated based on the movement speed (for example, movement distance per second (unit: mm)) and the rotation speed (for example, rotational speed per second (unit: times)) of the sensor portion 12 due to the pullback operation. The control unit 31, for example, calculates the frame pitch based on (movement speed/rotation speed).

Figure 9:
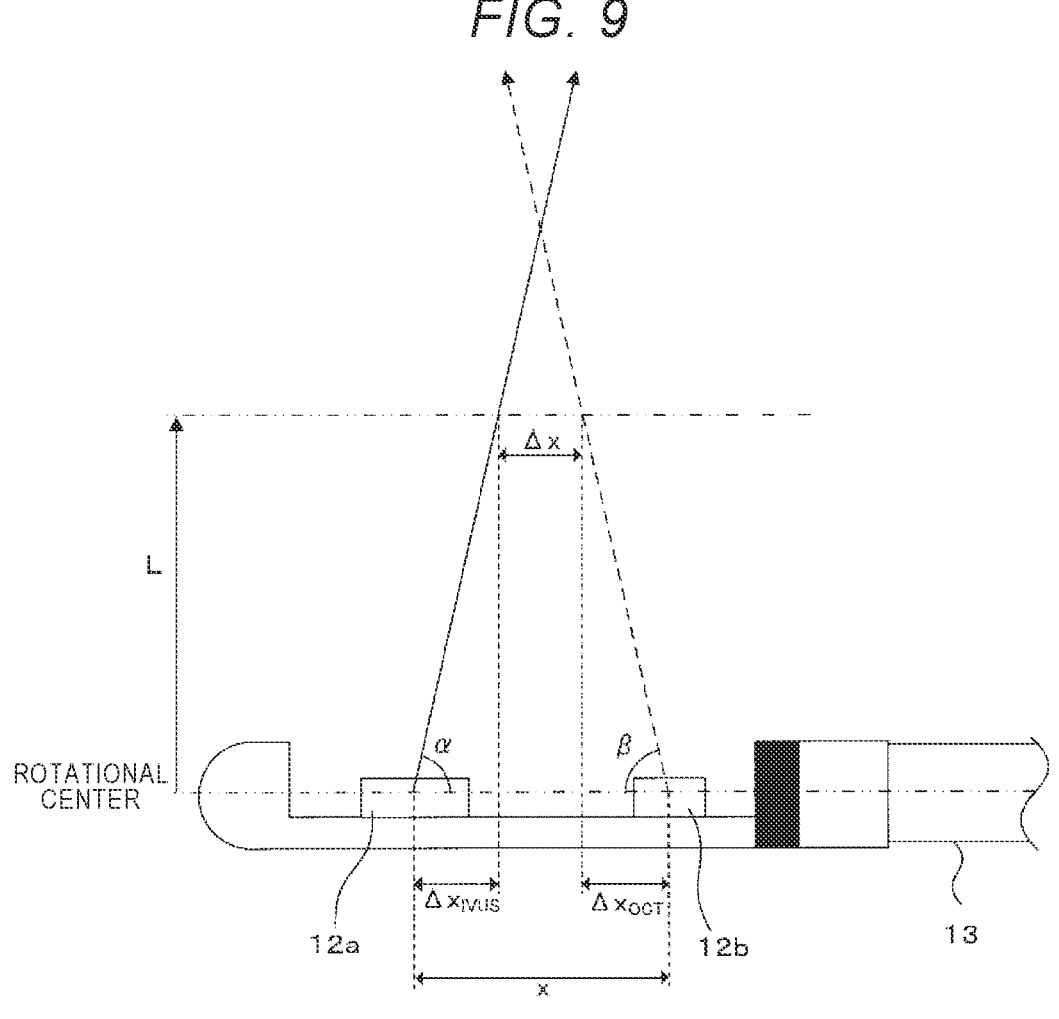
FIG. 9 is a diagram illustrating a method for calculating a deviation amount between observation positions corresponding to a distance from a rotational center of the sensor portion.

Next, the control unit 31 calculates the deviation amount between the observation positions at locations having respective distances from the rotational center of the sensor portion 12 (S14). Here, the control unit 31 calculates the deviation amount between the observation positions in the axial direction of the shaft 13, that is, the deviation amount between the emitting position of the ultrasound from the IVUS sensor 12a and the emitting position of the measurement light from the OCT sensor 12b. FIG. 9 is a diagram illustrating a method for calculating the deviation amount between the observation positions corresponding to the distance from the rotational center of the sensor portion 12. In FIG. 9, the deviation amount between the observation positions in an area where the distance from the rotational center of the sensor portion 12 is L is represented by $\Delta x$ (unit: mm). The deviation amount $\Delta x$ in the axial direction is expressed by the following Equation 1. x (unit: mm) is the deviation amount in the axial direction between the arrangement positions of the sensors 12a and 12b. In addition, $\Delta x_{IVUS}$ (unit: mm) is expressed by the following Equation 2, and $\Delta x_{OCT}$ (unit: mm) is expressed by the following Equation 3. Therefore, by substituting the Equations 2 and 3 into the Equation 1, an Equation 4 is obtained, and the deviation amount $\Delta x$ between the observation positions in the area where the distance from the rotational center of the sensor portion 12 is L is calculated using the Equation 4.

$$\Delta x = x - \Delta x_{IVUS} - \Delta x_{OCT} \qquad \text{(Equation 1)}$$

$$\Delta x_{IVUS} = L \times \cot \alpha \qquad \text{(Equation 2)}$$

$$\Delta x_{OCT} = L \times \cot \beta \qquad \text{(Equation 3)}$$

$$\Delta x = x - L \times (\cot \alpha + \cot \beta) \qquad \text{(Equation 4)}$$

Next, the control unit 31 calculates a correction amount (correction frame number) in the axial direction at locations having respective distances from the rotational center of the sensor portion 12 based on the deviation amount between the observation positions in the axial direction of the shaft 13 (S15). The correction frame number is calculated using the following Equation 5 based on the deviation amount between the observation positions in the axial direction calculated in S14 and the frame pitch calculated in S13.

$$\text{Correction frame number} = \Delta x / \text{frame pitch} \qquad \text{(Equation 5)}$$

The control unit 31 may calculate the distance L from the rotational center of respective locations where the deviation amount $\Delta x$ between observation positions is a multiple of the frame pitch, instead of calculating the deviation amount $\Delta x$ between the observation positions at respective distances from the rotational center of the sensor portion 12 and the correction frame number. For example, when the frame pitch is 0.1 mm, the distance L is calculated at which the deviation amount $\Delta x$ between the observation positions is 0.1 mm, 0.2 mm, 0.3 mm, . . . . In this case, 1, 2, 3, . . . can be specified as the correction frame number corresponding to the calculated distance L. FIG. 10 is a diagram illustrating an example of calculation results of the correction frame numbers corresponding to the distance L. In the example shown in FIG. 10, for example, the calculation results are shown when the movement speed of the sensor portion 12 is 10 mm/s, the rotation speed of the sensor portion 12 is 6000 rpm (100 fps), the distance x in the axial direction between the sensors 12a and 12b is 0.80 mm, the angle $\alpha$ of the ultrasound transmission and reception direction is 85°, and the angle $\beta$ of the measurement light transmission and reception direction is 84°. The correction frame number calculated in this way indicates a frame number of the OCT images when the observation target imaged in the IVUS image of one frame is imaged by the OCT sensor 12b, and by using such a correction frame number, the deviation between the observation positions in the axial direction can be corrected in frame pitch units.

Next, the control unit 31 calculates a correction amount (correction line number) in the circumferential direction based on the deviation amount between the observation positions in the rotation direction of the sensor portion 12 (S16). The correction line number is calculated based on the deviation amount in circumferential direction (angle $\varphi$) between the ultrasound transmission and reception direction of the IVUS sensor 12a and the measurement light transmission and reception direction of the OCT sensor 12b. The OCT image of one frame includes 512 line data arranged in the circumferential direction. Therefore, the control unit 31 can calculate the correction line number using the following Equation 6. Accordingly, when the transmission and reception directions are deviated by the angle $\varphi$, the OCT image is corrected forward by the correction line number, so that the observation position in the OCT image can be matched with the observation target in the IVUS image, and the correction for eliminating the deviation between the observation positions in the circumferential direction can be performed.

$$\text{Correction line number} = 512 \times \varphi / 360° \qquad \text{(Equation 6)}$$

The control unit 31 (image construction unit) constructs an OCT correction image in which the observation target is matched with that in the IVUS image based on the correction frame number corresponding to each distance calculated in S15 and the correction line number calculated in S16 (S17). For example, the control unit 31 subtracts the correction line number calculated in S16 from each line number of the optical line data. When the line number after subtraction is a negative number, 512 is added, so that each line number after subtraction has a value of 1 to 512. Accordingly, each line of the optical line data is associated with a respective line of the ultrasound line data, and according to the associated contents, the deviation between the observation positions in the circumferential direction with respect to the IVUS image is corrected. Then, the control unit 31 uses each line number of the optical line data after the subtraction to perform correction processing corresponding to the correction frame number calculated in S15, and constructs an OCT correction image of each frame. In the following description, construction processing of an OCT correction image of the nth frame will be described.

In the case of the calculation results shown in FIG. 10, for example, for an area where the distance from the rotational center is 0.78 mm (a location between mm and 1.04 mm), pixel values based on data values corresponding to the area where the distance from the rotational center is 0.78 mm are assigned in the optical line data of the (n−7)th frame. In addition, for an area where the distance from the rotational center is 0.78 mm to 1.30 mm (a location between 1.04 mm and 1.56 mm), pixel values based on data values corresponding to the area where the distance from the rotational center is 0.78 mm to 1.30 mm are assigned in the optical line data of the (n−6)th frame. By performing such processing for each area corresponding to the distance from the rotational center, the data of all lines of the optical line data and the data of all lines of the ultrasound line data are associated, respectively, and according to the associated contents, OCT images of frames corresponding to the deviation amount in each area can be synthesized to construct the OCT correction image of one frame. In an area farther from the rotational center than a position where the deviation amount between observation positions is 0, pixel values are assigned based on the data value of the optical line data of the (n+correction frame number)th frame. For example, among areas farther from the rotational center than the position where the deviation amount between the observation positions is 0, for an area where the calculated correction frame number is 1, pixel values based on the data value of the corresponding area in the optical line data of the (n+1)th frame are assigned. The OCT correction image constructed in this way is a tomographic image in which the deviation between the observation positions in the axial direction is corrected with respect to the IVUS image. The control unit 31 performs the correction processing in the rotation direction and the axial direction of the sensor portion 12 by the above-described processing, and interpolates the pixels between the lines by the interpolation processing on the optical line data to construct a two-dimensional OCT image (OCT correction image).

The control unit 31 performs the above-described correction processing, thereby constructing the OCT correction images of a plurality of frames based on the optical line data and generating the OCT correction image in which the observation position is matched with that in the IVUS image. The IVUS image and OCT correction image constructed by the above-described processing can be displayed on, for example, the display apparatus 4 and presented to an operator using the image diagnosis catheter 1.

In the present embodiment, as shown in FIGS. 2 and 6A, the sensors 12a and 12b are disposed such that the ultrasound transmission and reception direction of the IVUS sensor 12a and the measurement light transmission and reception direction of the OCT sensor 12b intersect, but the present embodiment is not limited to such a configuration. For example, also with a configuration in which the sensors 12a and 12b are disposed such that the ultrasound transmission and reception direction is a direction inclined toward the distal end side with respect to the radial direction of the shaft 13 and the measurement light transmission and reception direction is a direction inclined toward the proximal end side, the deviation between the observation positions in the IVUS image and the OCT image can be corrected by the similar processing.

Embodiment 2

An image diagnosis apparatus will be described in which all pieces of information used for correcting a tomographic image are measured when the image diagnosis catheter 1 is manufactured, and a code obtained by encoding the measured numerical values is added to the image diagnosis catheter 1. These pieces of information used in correction processing of the tomographic image include the distance x between the sensors 12a and 12b in an axial direction of the shaft 13, an ultrasound transmission and reception direction (angle $\alpha$) of the IVUS sensor 12a, a measurement light transmission and reception direction (angle $\beta$) of the OCT sensor 12b, and a deviation amount in rotation direction (angle $\varphi$) between the ultrasound transmission and reception direction and the measurement light transmission and reception direction of the sensor portion 12.

The image diagnosis apparatus 100 of the present embodiment can be implemented by devices similar to the devices in the image diagnosis apparatus 100 in Embodiment 1, and thus the descriptions of the similar configuration will be omitted. In the image diagnosis apparatus 100 of the present embodiment, a configuration of the image processing device 3 is slightly different from that in Embodiment 1, and thus only the different portions will be described.

Figure 11:
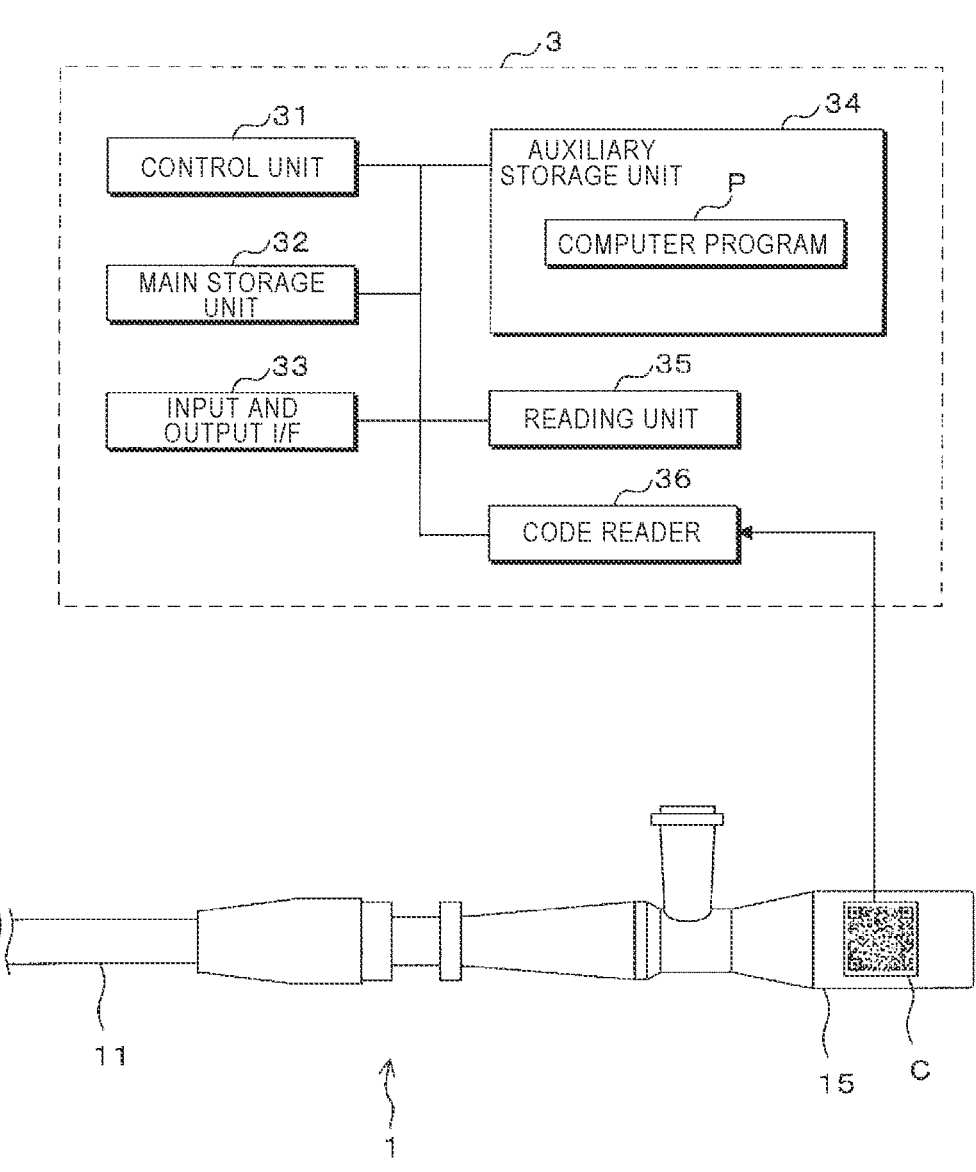
FIG. 11 is a block diagram showing a configuration example of an image processing device in Embodiment 2.

FIG. 11 is a block diagram showing a configuration example of the image processing device 3 in Embodiment 2. The image processing device 3 of the present embodiment includes a code reader 36 in addition to the configuration of the image processing device 3 in Embodiment 1 shown in FIG. 5. The code reader 36 is a device that reads a one-dimensional code such as a bar code and a two-dimensional code such as a QR Code®, decodes the read code to acquire code information, and sends the obtained code information to the control unit 31.

In the image diagnosis apparatus 100 of the present embodiment, the above-described information (x, $\alpha$, $\beta$, and $\varphi$) used in the correction processing of the tomographic image are measured in the process for manufacturing the image diagnosis catheter 1, and each of the measured numerical values, and a serial number applied to the image diagnosis catheter 1 are coded. In the example shown in FIG. 11, a QR code C is applied to the connector portion 15. The code C may be printed directly on the connector portion 15, or a seal printed with the code C may be attached to the connector portion 15. In the image diagnosis apparatus 100 having such a configuration, for example, an operator reads, by the code reader 36, the code C when connecting the image diagnosis catheter 1 to the MDU 2 via the connector portion 15, so that the image processing device 3 acquires the information (x, $\alpha$, $\beta$, and $\varphi$) used in the correction processing of the tomographic image.

FIG. 12 is a flowchart showing an example of a tomographic image correction processing procedure in Embodiment 2. The processing shown in FIG. 12 is obtained by adding S21 before S11 in the processing shown in FIG. 8. Descriptions of the same steps as in FIG. 8 will be omitted. In the image diagnosis apparatus 100 of the present embodiment, the control unit 31 of the image processing device 3 first reads code information from the code C by the code reader 36 (S21). The code information includes the numerical values (x, $\alpha$, $\beta$, and $\varphi$) measured during the process for manufacturing the image diagnosis catheter 1 and the serial number of the image diagnosis catheter 1, and each piece of read information is stored in the main storage unit 32.

Thereafter, the intravascular imaging process is started by the intravascular examination device 101, and the control unit 31 executes the processing S11 and subsequence steps. In the present embodiment, each piece of information read from the code C is used when calculating the frame pitch at the time of imaging in S13, when calculating the deviation amount between the observation positions in the axial direction of the shaft 13 and the correction frame number in S14 and S15, and when calculating the correction line number in the rotation direction of the sensor portion 12 in S16.

By the above-described processing, in the present embodiment, an OCT correction image can also be constructed in which the deviations in the axial direction and the rotation direction of the sensor portion 12 between the observation position of the IVUS sensor 12a and the observation position of the OCT sensor 12b are corrected, and the observation position is matched with that in the IVUS image.

In the present embodiment, the same effects as those in the above-described Embodiment 1 can be obtained. In addition, in the present embodiment, the distance x between the sensors 12a and 12b, the ultrasound transmission and reception direction (angle α) of the IVUS sensor 12a, the measurement light transmission and reception direction (angle β) of the OCT sensor 12b, and the deviation amount in rotation direction (angle φ) between the ultrasound transmission and reception direction and the measurement light transmission and reception direction of the sensor portion 12 are measured during the process for manufacturing the image diagnosis catheter 1, coded, and applied to the image diagnosis catheter 1 (for example, the connector portion 15). Therefore, the image processing device 3 can acquire each piece of information to be used in the correction processing to be performed on the tomographic image by reading the code C applied to the image diagnosis catheter 1 by the code reader 36. These pieces of information include an attachment error (individual difference) that occurs in each catheter 1 during the manufacturing process. Therefore, it is possible to perform the correction processing with relatively high accuracy by applying the code C to the catheter 1. In the present embodiment, it is also possible to apply modifications described as appropriate in the above-described Embodiment 1. For example, processing may be performed to construct an IVUS correction image in which the observation target is matched with that in the OCT image based on the ultrasound line data, instead of constructing the OCT correction image in which the observation target is matched with that in the IVUS image based on the optical line data. With such a configuration, the same effects as in the present embodiment can also be obtained.

Embodiment 3

Regarding the image diagnosis apparatus 100 in Embodiment 2, an image diagnosis apparatus in which the image processing device 3 acquires each piece of information used when correcting a tomographic image from a server will be described. The image diagnosis apparatus 100 of the present embodiment can be implemented by devices similar to the devices in the image diagnosis apparatus 100 in Embodiment 1, and thus the descriptions of the similar configuration will be omitted. In the image diagnosis apparatus 100 of the present embodiment, the configuration of the image processing device 3 is slightly different from that in Embodiment 2. In the present embodiment, these pieces of information (x, α, β, and φ) used when correcting the tomographic image are managed by a server connected to a network such as the Internet. Therefore, the image processing device 3 can perform correction processing similar to that in Embodiments 1 and 2 by acquiring these pieces of information used in the correction processing of the tomographic image from the server via the network.

Figure 13:
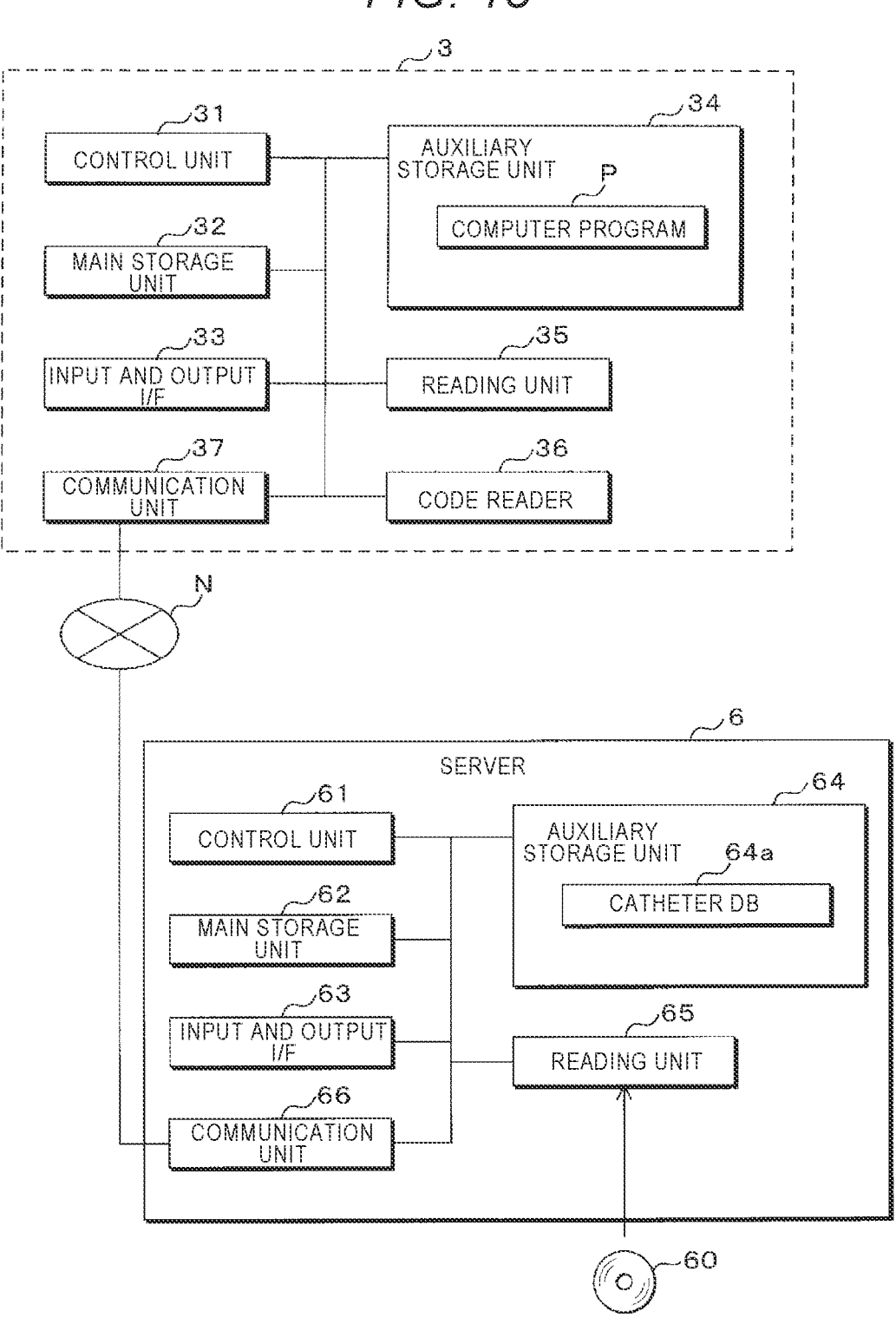
FIG. 13 is a block diagram showing a configuration example of an image processing device and a server in Embodiment 3.

FIG. 13 is a block diagram showing a configuration example of the image processing device 3 and a server 6 in Embodiment 3. The image processing device 3 of the present embodiment includes a communication unit 37 in addition to the configuration of the image processing device 3 in Embodiment 2 shown in FIG. 11. The communication unit 37 is a communication module that connects the image processing device 3 to a network N by wired communication or wireless communication, and transmits information to and receives information from other devices via the network N.

The server 6 can include, for example, a server computer or a personal computer. A plurality of servers 6 may be provided for distributed processing, and the server 6 may be implemented by a plurality of virtual machines provided in one server, or may be implemented using a cloud server. The server 6 can include a control unit 61, a main storage unit 62, an input and output I/F 63, an auxiliary storage unit 64, a reading unit 65, and a communication unit 66. The control unit 61, the main storage unit 62, the input and output I/F 63, the auxiliary storage unit 64, the reading unit 65, and the communication unit 66 of the server 6 have the same configurations as the control unit 31, the main storage unit 32, the input and output I/F 33, the auxiliary storage unit 34, the reading unit 35, and the communication unit 37 of the image processing device 3, respectively, and thus descriptions of the configurations of the control unit 61, the main storage unit 62, the input and output I/F 63, the auxillary storage unit 64, the reading unit 65, and the communication unit 66 of the server 6 will be omitted. The auxiliary storage unit 64 of the server 6 stores the computer program executed by the control unit 61 as well as a catheter database (DB) 64a, which will be described later. The catheter DB 64a may be stored in another storage device connected to the server 6, or may be stored in another storage device with which the server 6 can communicate.

FIG. 14 is a schematic diagram showing a configuration example of the catheter DB 64a. The catheter DB 64a stores the numerical values (x, α, β, and φ) measured during the process for manufacturing the image diagnosis catheter 1 in association with the serial number applied to the image diagnosis catheter 1. Specifically, the distance x in the axial direction between the sensors 12a and 12b attached to the image diagnosis catheter 1, the angle α of the ultrasound transmission and reception direction of the IVUS sensor 12a, the angle β of the measurement light transmission and reception direction of the OCT sensor 12b, and the deviation amount in rotation direction (angle φ) between the ultrasound transmission and reception direction and measurement light transmission and reception direction of the sensor portion 12 are registered.

In the image diagnosis apparatus 100 having the above-described configuration, these pieces of information (x, α, β, and φ) used in the correction processing of the tomographic image are measured in the process for manufacturing the image diagnosis catheter 1, and each of the measured numerical values is registered in the server 6 together with the serial number applied to the image diagnosis catheter 1. On the other hand, the serial number applied to the image diagnosis catheter 1 is coded, and the code C is applied to the connector portion 15 in the same manner as in FIG. 11. In the image diagnosis apparatus 100 of the present embodiment, the operator also reads, by the code reader 36, the code C when connecting the image diagnosis catheter 1 to the MDU 2 via the connector portion 15. Accordingly, the image processing device 3 acquires the serial number of the image diagnosis catheter 1, and acquires these pieces of information (x, a, 13, and (p) used in the correction processing of the tomographic image from the server 6 based on the serial number.

Figure 15:
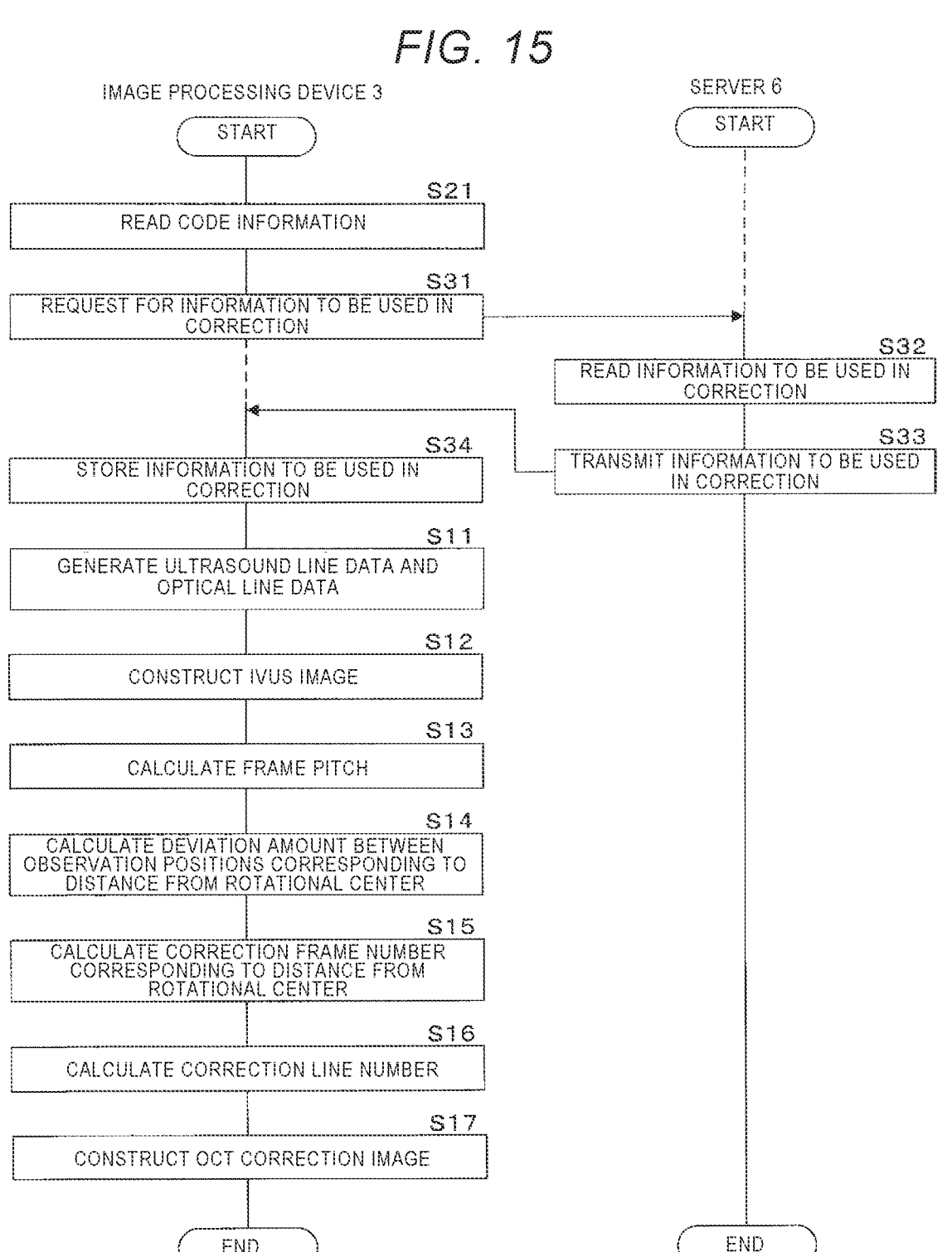
FIG. 15 is a flowchart showing an example of a tomographic image correction processing procedure in Embodiment 3.

FIG. 15 is a flowchart showing an example of a tomographic image correction processing procedure in Embodiment 3. The processing shown in FIG. 15 is obtained by adding sS31 to S34 between S21 and S11 in the processing shown in FIG. 12. Descriptions of the same processes as in FIG. 12 will be omitted. In FIG. 15, processing performed by the image processing device 3 is shown on a left side, and processing performed by the server 6 is shown on a right side. In the image diagnosis apparatus 100 of the present embodiment, the control unit 31 of the image processing device 3 first reads code information from the code C by the code reader 36 (S21). The code information here is the serial number of the image diagnosis catheter 1, and based on the read serial number, the control unit 31 requests the server 6 for these pieces of information (x, $\alpha$, $\beta$, and $\varphi$) to be used in the correction processing to be performed on the tomographic image acquired using the image diagnosis catheter 1 here (S31).

When the serial number of the image diagnosis catheter 1 is acquired from the image processing device 3, the control unit 61 of the server 6 reads each piece of information (x, $\alpha$, $\beta$, and $\varphi$) corresponding to the serial number from the catheter DB 64a (S32). The control unit 61 then transmits each piece of read information (x, $\alpha$, $\beta$, and $\varphi$) to the image processing device 3 via the network N (S33). The control unit 31 of the image processing device 3 stores each piece of information (x, $\alpha$, $\beta$, and $\varphi$) acquired from the server 6 in the main storage unit 32 (S34).

Thereafter, the intravascular imaging process is started by the intravascular examination device 101, and the control unit 31 executes the processing S11 and subsequence processes. In the present embodiment, each piece of information acquired from the server 6 is used when calculating the frame pitch at the time of imaging in S13, when calculating the deviation amount between the observation positions in the axial direction of the shaft 13 and the correction frame number in S14 and S15, and when calculating the correction line number in the rotation direction of the sensor portion 12 in S16. By the above-described processing, in the present embodiment, an OCT correction image also can be constructed in which the deviations in the axial direction and the rotation direction of the sensor portion 12 between the observation position of the IVUS sensor 12a and the observation position of the OCT sensor 12b are corrected, and the observation position is matched with that in the IVUS image.

In the present embodiment, the same effects as those in the above-described embodiments can be obtained. In addition, in the present embodiment, each piece of information (x, $\alpha$, $\beta$, and $\varphi$) used in the correction processing performed on the tomographic image is managed by the server 6 corresponding to the serial number of the image diagnosis catheter 1. Therefore, the image processing device 3 can acquire each piece of information to be used in the correction processing to be performed on the tomographic image from the server 6. Accordingly, in the present embodiment, it is also possible to perform correction processing with relatively high accuracy and provide an IVUS image and an OCT image in which the observation targets are matched. In the present embodiment, it is also possible to apply modifications described as appropriate in the above-described embodiments.

Embodiment 4

The image diagnosis apparatus 100 in which the image processing device 3 specifies each piece of information used in correction processing to be performed on an IVUS image or OCT image based on the IVUS image and the OCT image will be described. The image diagnosis apparatus 100 of the present embodiment can be implemented by devices similar to the devices in the image diagnosis apparatus 100 in Embodiment 1, and thus the descriptions of the similar configuration will be omitted. In the image diagnosis apparatus 100 of the present embodiment, the image processing device 3 stores a training model 34M in the auxiliary storage unit 34 in addition to the configuration of the image processing device 3 in Embodiment 1 shown in FIG. 5.

Figure 16:
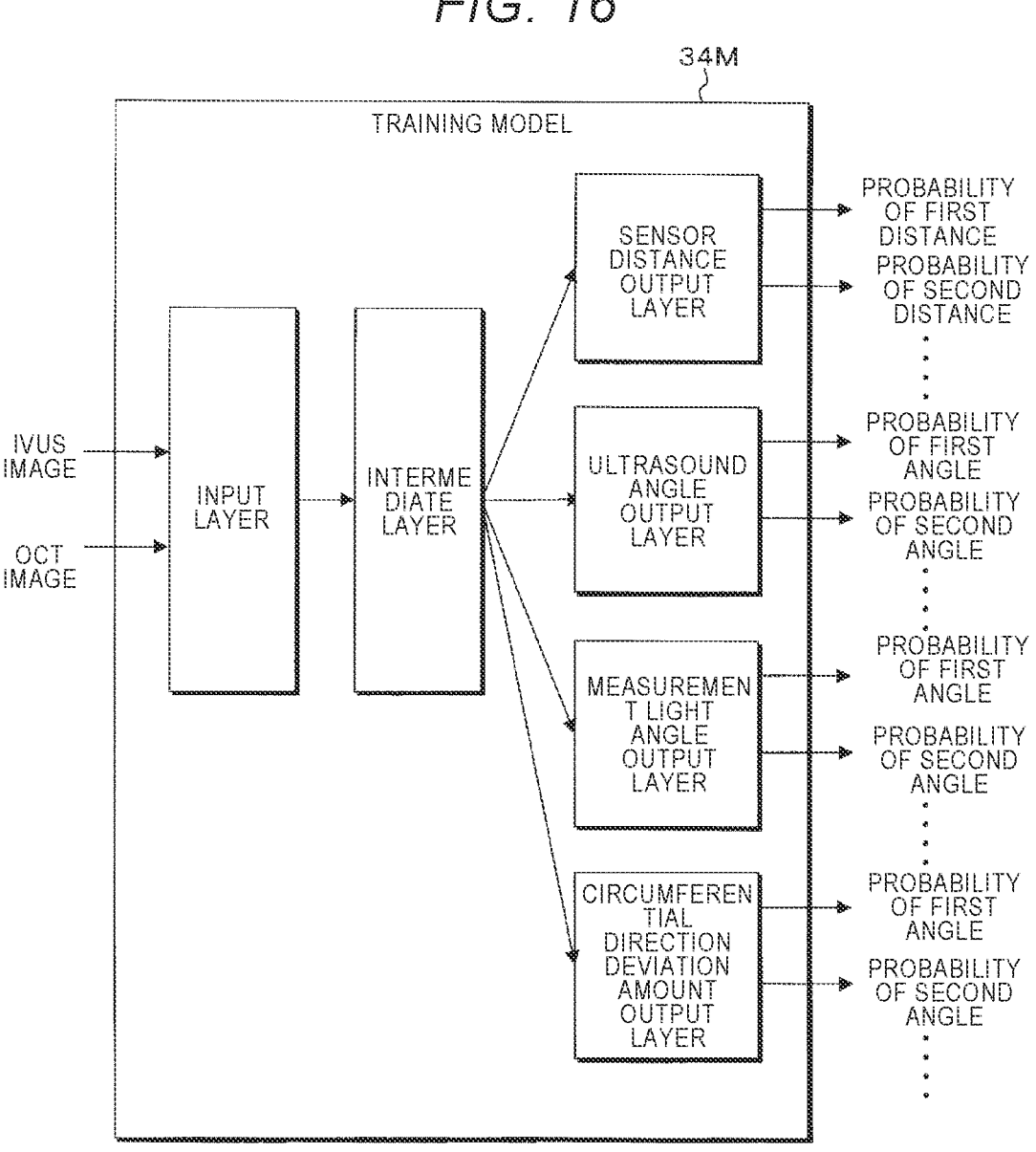
FIG. 16 is a schematic diagram showing a configuration example of a training model.

FIG. 16 is a schematic diagram showing a configuration example of the training model 34M. The training model 34M is a machine learning model that inputs the IVUS image and the OCT image generated by the image processing device 3 based on the ultrasound line data and the optical line data obtained using the image diagnosis catheter 1, and outputs the information used in the correction processing to be performed on the IVUS image or OCT image. In the image diagnosis catheter 1, these pieces of information used in the correction processing include the distance x between the sensors 12a and 12b in the axial direction of the shaft 13, the ultrasound transmission and reception direction (angle $\alpha$), the measurement light transmission and reception direction (angle $\beta$), and the deviation amount in rotation direction (angle $\varphi$) between the ultrasound transmission and reception direction and the measurement light transmission and reception direction of the sensor portion 12. The training model 34M outputs a probability of an option set in advance for each piece of the information (x, $\alpha$, $\beta$, and $\varphi$).

The training model 34M can include, for example, a convolutional neural network (CNN), which is a neural network generated by deep learning. In addition to the CNN, the training model 34M may include algorithms such as a recurrent neural network (RNN), a generative adversarial network (GAN), a decision tree, a random forest, and a support vector machine (SVM), or may be obtained by combining a plurality of algorithms. The image processing device 3 performs machine learning using predetermined training data to generate the training model 34M in advance. Then, the image processing device 3 inputs the IVUS image and the OCT image in the training model 34M, and obtains the information used in the correction processing to be performed on the IVUS image or OCT image.

For example, the IVUS image and the OCT image acquired by one pullback operation by the MDU 2 are input into the training model 34M. An IVUS image and an OCT image of one frame acquired at the same timing may be input into the training model 34M, and an IVUS image and an OCT image acquired in time series may be input sequentially into the training model 34M. The training model 34m includes an input layer in which the IVUS image and the OCT image are input, an intermediate layer that extracts feature data from input information, and output layers that output each piece of information used in the correction processing. Regarding the output layers, one output layer is provided for each piece of information (x, $\alpha$, $\beta$, and $\varphi$).

The input layer can include a plurality of input nodes, and each pixel in the IVUS image and the OCT image is input to a respective input node. The intermediate layer calculates output values by performing computations for filtering processing, compression processing, and the like on the tomographic image input via the input layer using predetermined functions and thresholds, and outputs the calculated output values to the output layers. When a plurality of intermediate layers are provided, for nodes in each layer, output values based on the input tomographic image are calculated using the functions and thresholds between the layers, and the calculated output values are input to nodes in subsequent layers sequentially. The intermediate layers give finally calculated output values to the output layers by inputting the output values of the nodes in the layers to the nodes in the subsequent layers sequentially.

The training model 34M can include a sensor distance output layer, an ultrasound angle output layer, a measurement light angle output layer, and a circumferential direction deviation amount output layer as the output layers. The sensor distance output layer outputs the distance x between the sensors 12a and 12B, the ultrasound angle output layer outputs the ultrasound transmission and reception direction (angle α), the measurement light angle output layer outputs the measurement light transmission and reception direction (angle β), and the circumferential direction deviation amount output layer outputs the deviation amount in rotation direction (angle φ) between the ultrasound transmission and reception direction and the measurement light transmission and reception direction. The sensor distance output layer includes a plurality of output nodes associated with distances (first distance, second distance, and the like) prepared as the options, and outputs probabilities at which the associated distances are to be determined from the output nodes. The output value from each output node in the sensor distance output layer can be, for example, a value between 0 and 1, and a sum of the probabilities output from the output nodes is 1.0 (100%). Similarly, each of the ultrasound angle output layer, the measurement light angle output layer, and the circumferential direction deviation amount output layer includes a plurality of output nodes associated with angles (first angle, second angle, and the like) prepared as options, and outputs probabilities at which the associated angles are to be determined from the output nodes. In each of the ultrasound angle output layer, the measurement light angle output layer, and the circumferential direction deviation amount output layer, the output value from each output node can be, for example, a value between 0 and 1, and a sum of the probabilities output from the output nodes is 1.0 (100%). The angles set as the options for the ultrasound angle output layer, the measurement light angle output layer, and the circumferential direction deviation amount output layer are angles different from each other. With the above-described configuration, when the IVUS image and the OCT image are input, the training model 34M outputs each piece of information (x, α, β, and φ) on the image diagnosis catheter 1 by which the IVUS image and the OCT image are captured.

When using the above-described training model 34M, the image processing device 3 specifies a distance associated with an output node that outputs a maximum output value (determination probability) among the output values from the sensor distance output layer as the distance between the sensors in the image diagnosis catheter 1. In addition, an angle associated with an output node that outputs a maximum output value among the output values from the ultrasound angle output layer is specified as an ultrasound transmission and reception angle of the IVUS sensor 12a. In addition, an angle associated with an output node that outputs a maximum output value among the output values from the measurement light angle output layer is specified as the measurement light transmission and reception angle of the OCT sensor 12b. Furthermore, an angle associated with an output node that outputs a maximum output value among the output values from the circumferential direction deviation amount output layer is specified as the deviation amount in circumferential direction between the ultrasound and the measurement light. A selection layer in which an option having a highest probability is selected and output may be provided at a subsequent stage of each output layer. In this case, each output layer has a configuration including one output node that outputs the option (distance or angle) having the highest determination probability.

The training model 34M can be generated by preparing training data and performing machine learning on an untrained training model using this training data. The training data includes the IVUS image and the OCT image acquired using the image diagnosis catheter 1 and each piece of information (x, α, β, and φ) (correct labels) measured during the process for manufacturing the image diagnosis catheter 1, for example. When the IVUS image and the OCT image included in the training data are input to the training model 34M, the training model 34M is trained such that the output value from the output node corresponding to each correct label (each piece of information) included in the training data approaches 1 and the output values from the other output nodes approach 0 in respective output layers. Specifically, the training model 34M performs the computations in the intermediate layer based on the input IVUS image and the OCT image, and calculates the output values from the output nodes of each output layer. Then, the training model 34M compares the calculated output values of the output nodes with a value corresponding to the correct label (1 for the output node corresponding to the correct value, and 0 for the other output nodes), and optimizes parameters used in the computational processing in the intermediate layer such that each output value approaches the value corresponding to the correct label. The parameters can be, for example, weights (coupling coefficients) between neurons. A parameter optimization method is not particularly limited, and a gradient descent method, error back-propagation method, or the like can be used.

Training of the training model 34M may be performed by other training devices. The trained training model 34M generated by being trained in another training device is downloaded from the training device to the image processing device 3 via the network or via the recording medium 30, for example, and stored in the auxiliary storage unit 34.

Figure 17:
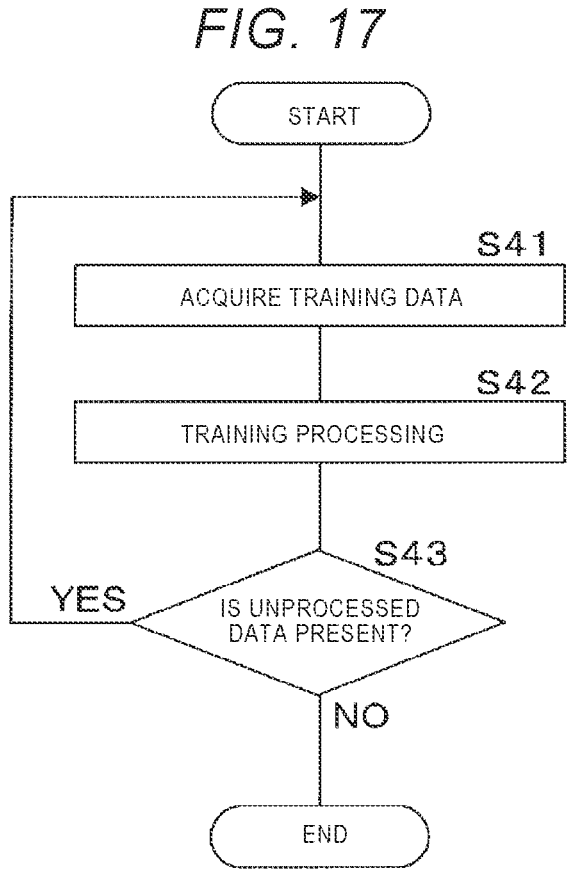
FIG. 17 is a flowchart showing an example of a training model generation processing procedure.

Processing for generating the training model 34M by training using the training data will be described below. FIG. 17 is a flowchart showing an example of a generation processing procedure of the training model 34M. The following processing is performed by the control unit 31 of the image processing device 3 according to the computer program P stored in the auxiliary storage unit 34, and may be performed by another training device.

The control unit 31 of the image processing device 3 acquires the training data to which each piece of correct information (x, α, β, and φ) is added, from an IVUS image and an OCT image (S41). As the IVUS image and the OCT image used for the training data, an IVUS image and an OCT image captured during a catheter treatment can be used. As the correct information, information measured during the process for manufacturing the image diagnosis catheter 1 by which the IVUS image and the OCT image are captured can be used. As the training data, the IVUS image and the OCT image used for the training data, and each piece of information on the image diagnosis catheter 1 may be prepared in advance and registered in a training data database (DB). In this case, the control unit 31 may acquire the training data from the training data DB.

The control unit 31 performs the training processing of the training model 34M using the acquired training data (S42). Here, the control unit 31 inputs the IVUS image and the OCT image included in the training data to the training model 34M, and acquires the output values related to these pieces of information on the distance x between the sensors, the ultrasound angle $\alpha$, the measurement light angle $\beta$, and the circumferential direction deviation amount $\varphi$. The control unit 31 compares the output value related to each piece of output information with the value (0 or 1) corresponding to a respective piece of correct information, and optimizes the parameters used in the computational processing in the intermediate layer such that the two approximate each other. Specifically, the control unit 31 trains the training model 34M such that the output value from the output node corresponding to each correct value approaches 1 and the output values from the other output nodes approach 0 in respective output layers.

The control unit 31 determines whether unprocessed data is present (S43). For example, when the training data is registered in the training data DB in advance, the control unit 31 determines whether unprocessed training data is present in the training data stored in the training data DB. When determining that unprocessed data is present (YES in S43), the control unit 31 returns to the processing of S41, and performs the processing of S41 to S42 based on the unprocessed training data. When determining that unprocessed data is not present (NO in S43), the control unit 31 ends the series of processing.

With the above-described processing, the training model 34M is obtained, which is trained to output each piece of information (x, $\alpha$, $\beta$, and $\varphi$) on the image diagnosis catheter 1 used in capturing the IVUS image and the OCT image by inputting the IVUS image and the OCT image. The training model 34M can be further optimized by repeating the training processing using the above-described training data. In addition, the training model 34M that was trained can be retrained by performing the above-described processing, and in this case, the training model 34M having higher determination accuracy can be obtained.

In the image diagnosis apparatus 100 of the present embodiment, after acquiring the IVUS image and the OCT image using the image diagnosis catheter 1, each piece of information (x, $\alpha$, $\beta$, and $\varphi$) on the image diagnosis catheter 1 is specified from the acquired IVUS image and the acquired OCT image using the training model 34M. Then, the image processing device 3 uses each piece of specified information (x, $\alpha$, $\beta$, and $\varphi$) to perform the correction processing on the IVUS image or the OCT image, thereby matching the observation target in the IVUS image with that in the OCT image.

Figure 18:
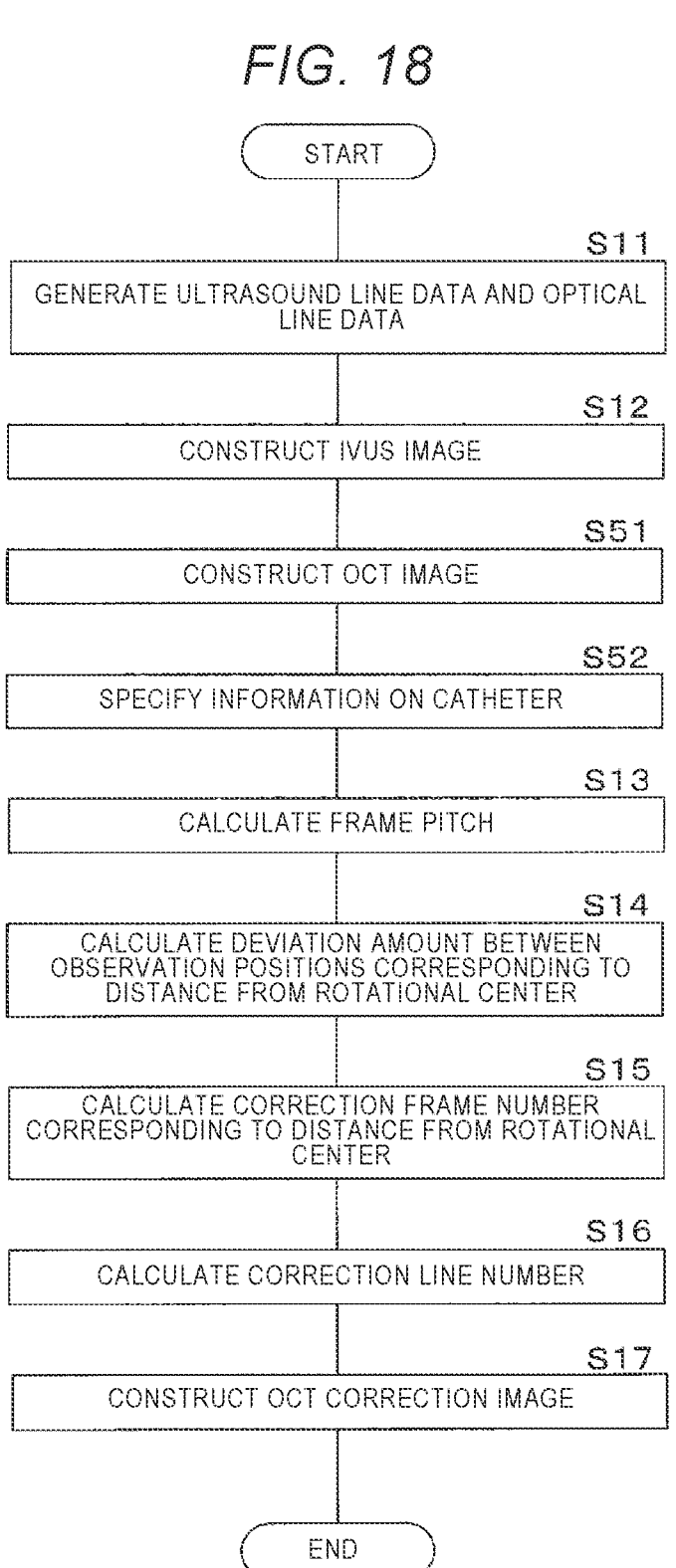
FIG. 18 is a flowchart showing an example of a tomographic image correction processing procedure in Embodiment 4.

FIG. 18 is a flowchart showing an example of a tomographic image correction processing procedure in Embodiment 4. The processing shown in FIG. 18 is obtained by adding S51 to S52 between S12 and S13 in the processing shown in FIG. 8. Descriptions of the same steps as in FIG. 8 will be omitted. In the image processing device 3 of the present embodiment, the control unit 31 constructs a two-dimensional OCT image by interpolating the pixels by interpolation processing for the optical line data acquired in S11 after performing the processing of S11 to S12 shown in FIG. 8 (S51). The IVUS image and the OCT image here are images in which observation positions thereof are deviated.

Next, the control unit 31 inputs the IVUS image constructed in S12 and the OCT image constructed in S51 to the training model 34M, and specifies each piece of information (x, $\alpha$, $\beta$, and $\varphi$) on the image diagnosis catheter 1 by which the IVUS image and the OCT image are captured based on the output values from the training model 34M (S52). For example, the control unit 31 specifies the output node that outputs the maximum output value among the output nodes of each output layer in the training model 34M, and specifies the value (distance or angle) associated with the specified output node as each piece of information on the image diagnosis catheter 1. Each piece of information (x, $\alpha$, $\beta$, and $\varphi$) specified in this way is stored in the main storage unit 32, for example.

Thereafter, the control unit 31 executes the processing S11 and subsequence processes. In the present embodiment, each piece of the information specified by using the training model 34M is used when calculating the frame pitch at the time of imaging in S13, when calculating the deviation amount between the observation positions in the axial direction of the shaft 13 and the correction frame number in S14 and S15, and when calculating the correction line number in the rotation direction of the sensor portion 12 in S16. By the above-described processing, also in the present embodiment, the deviation between the observation positions of the IVUS sensor 12a and the OCT sensor 12b are corrected, and an IVUS image and an OCT correction image in which the observation positions are matched can be provided.

In the present embodiment, the same effects as those in the above-described embodiments can be obtained. In addition, in the present embodiment, each piece of information (x, $\alpha$, $\beta$, and $\varphi$) used in the correction processing to be performed on the IVUS image or the OCT image is specified from the IVUS image and the OCT image using the training model 34M. Therefore, by performing the correction processing using such information, it is possible to construct an OCT correction image in which the observation position is matched with that in the IVUS image. In the present embodiment, it is also possible to apply modifications described as appropriate in the above-described embodiments.

In the present embodiment, the image processing device 3 locally performs the processing of specifying each piece of information (each piece of information used in the correction processing) in the image diagnosis catheter 1 using the training model 34M, but the present disclosure is not limited to this configuration. For example, a server that performs specific processing for each piece of information using the training model 34M may be provided. In this case, the image processing device 3 may transmit the IVUS image and the OCT image to the server, and acquire each piece of information specified from the IVUS image and the OCT image by the server. With such a configuration, the same processing as in the present embodiment is also possible, and the same effects also can be obtained.

In the present embodiment, the training model 34M may output the correction frame number and the correction line number (correction amounts) used in the correction processing instead of outputting each piece of information (x, $\alpha$, $\beta$, and $\varphi$) used in the correction processing when the IVUS image and the OCT image are input. In this case, the image processing device 3 can use the training model 34M to specify the correction amounts to be used in the correction processing, and perform the correction processing using the specified correction amounts, thereby generating the corrected IVUS correction image or OCT correction image. In addition, the training model 34M may output an IVUS correction image or OCT correction image on which the correction processing is performed when the IVUS image and the OCT image are input. In this case, the image processing device 3 can use the training model 34M, thereby generating the corrected IVUS correction image or OCT correction image.

Embodiment 5

In the image diagnosis apparatus 100 of the above-described Embodiments 1 to 4, the image processing device 3 constructs the OCT correction image in which the observation target is matched with that in the IVUS image. In the present embodiment, the image processing device 3 that constructs an IVUS correction image or OCT correction image in which an observation target is matched with the position of the marker 12c (contrast marker) visualized on an angiographic image will be described. The image diagnosis apparatus 100 of the present embodiment can be implemented by devices similar to the devices in the image diagnosis apparatus 100 in Embodiment 1, and thus the descriptions of the similar configuration will be omitted. In the following description, a configuration in which the image diagnosis catheter 1 includes both the IVUS sensor 12a and the OCT sensor 12b will be described as an example, but the image diagnosis catheter 1 of the present embodiment may include only the IVUS sensor 12a, or may include the OCT sensor 12b only. In the following description, processing of constructing the IVUS correction image in which the observation target is matched with the marker 12c on the angiographic image will be described, but by similar processing, it is also possible to construct an OCT correction image in which an observation target is matched with the marker 12c on the angiographic image.

Figure 19:
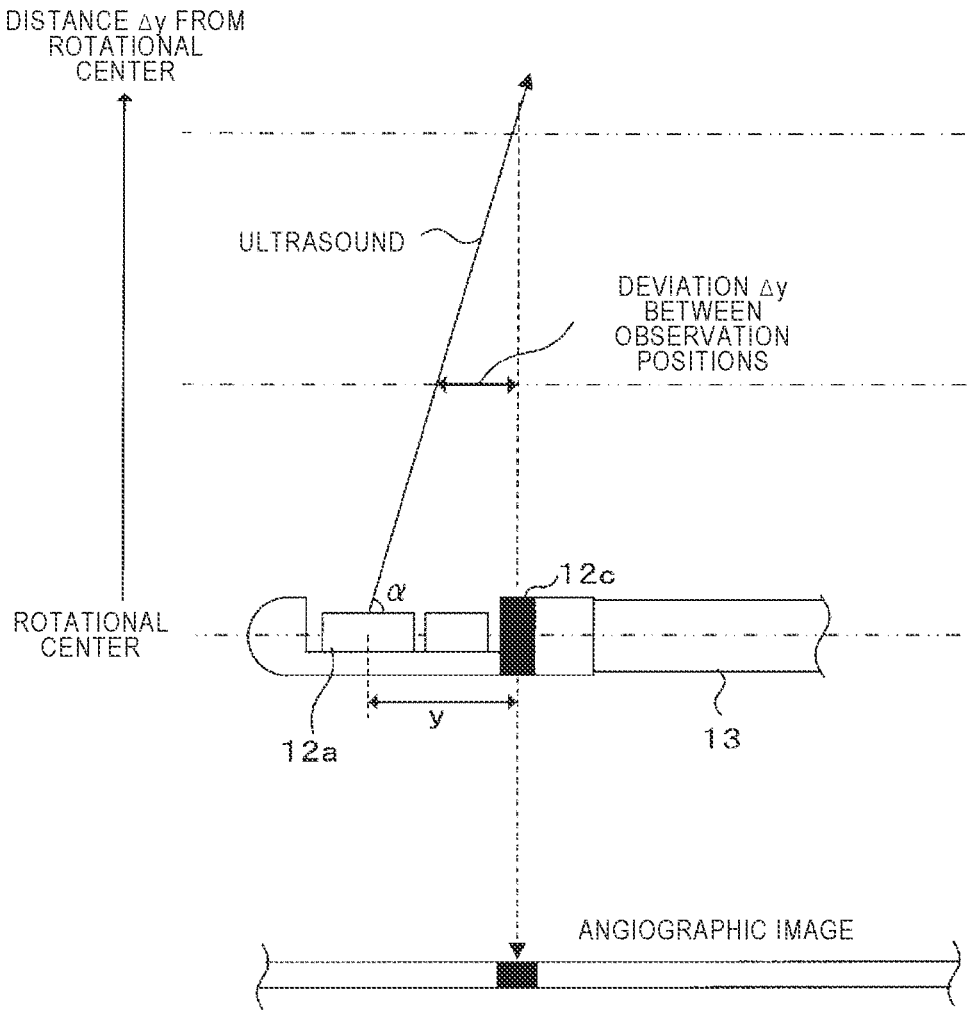
FIG. 19 is a diagram illustrating a deviation of an observation position of an IVUS sensor with respect to a marker.

FIG. 19 is a diagram illustrating a deviation of an observation position of the IVUS sensor 12a with respect to the marker 12c. FIG. 19 shows a state where the sensor portion 12 is seen from the radial direction of the shaft 13. When the image diagnosis catheter 1 is imaged by the angiography device 102, an angiographic image in which the marker 12c is visualized as shown in a lower diagram of FIG. 19 is obtained. In the sensor portion 12 in the present embodiment, the IVUS sensor 12a uses a direction having the angle α with respect to the direction of the proximal end side on the central axis of the shaft 13 as the ultrasound transmission and reception direction. Therefore, as shown in FIG. 19, a path of the ultrasound and a contrast enhancement range of the marker 12c intersect with each other, and at locations other than the intersection position, the observation position of the IVUS sensor 12a deviates in the axial direction of the shaft 13 with respect to the position of the marker 12c. The deviation of the observation position of the IVUS sensor 12a with respect to the position of the marker 12c varies depending on a distance y between the arrangement positions of the IVUS sensor 12a and the marker 12c, the attachment angle of the IVUS sensors 12a (the angle α of the ultrasound transmission and reception direction), and the distance L from the rotational center of the sensor portion 12.

Figure 20:
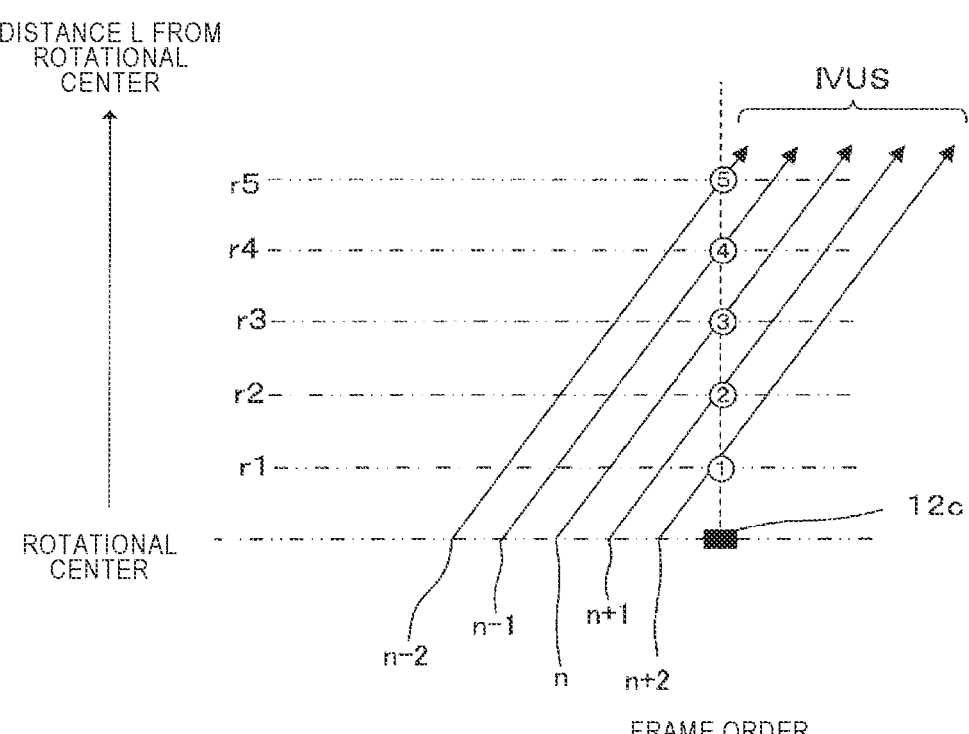
FIG. 20 is a diagram illustrating processing of correcting the deviation of the observation position.

When constructing an IVUS image from the ultrasound line data, the image processing device 3 of the present embodiment constructs an IVUS correction image obtained by correcting the deviation of the observation position of the IVUS sensor 12a with respect to the position of the marker 12c as described above. FIGS. 20 and 21 are diagrams illustrating processing of correcting the deviation of the observation position. FIG. 20 is a diagram illustrating deviations of observation positions of the IVUS sensor 12a in the axial direction of the shaft 13, and FIG. 21 is a diagram illustrating an IVUS correction image in which the observation positions are aligned with the position of the marker 12c. FIG. 20 shows a position of the marker 12c at the imaging timing of an IVUS image of an nth frame, and FIG. 20 show positions at distances r1 to r5 from the rotational center of the sensor portion 12 in the position (contrast enhancement range) of the marker 12c in the nth frame. FIG. 20 shows that the IVUS sensor 12a observes the observation position 5 in an (n−2)th frame, observes the observation position 4 in an (n−1)th frame, observes the observation position 3 in the nth frame, observes the observation position 2 in an (n+1)th frame, and observes the observation position 1 in an (n+2)th frame.

In such a situation, as shown in an upper part of FIG. 21, in these IVUS images, the observation position 5 is imaged in the (n−2)th frame, the observation position 4 is imaged in the (n−1)th frame, the observation position 3 is imaged in the nth frame, the observation position 2 is imaged in the (n+1)th frame, and the observation position 1 is imaged in the (n+2)th frame. That is, in the example shown in FIGS. 20 and 21, an observation timing of the IVUS sensor 12a for the observation position 5 is two frames before an arrival timing of the marker 12c, and an observation timing of the IVUS sensor 12a for the observation position 4 is one frame before the arrival timing of the marker 12c. In addition, an observation timing of the IVUS sensor 12a for the observation position 2 is one frame later the arrival timing of the marker 12c, and an observation timing of the IVUS sensor 12a for the observation position 1 is two frames later the arrival timing of the marker 12c. Therefore, as shown in a lower part of FIG. 21, the image processing device 3 can synthesize each area (areas corresponding to the distances from the rotational center) in the IVUS images of a plurality of frames to construct an IVUS image of one frame, thereby generating the IVUS correction image in which the observation positions are matched with the position of the marker 12c.

Figure 22:
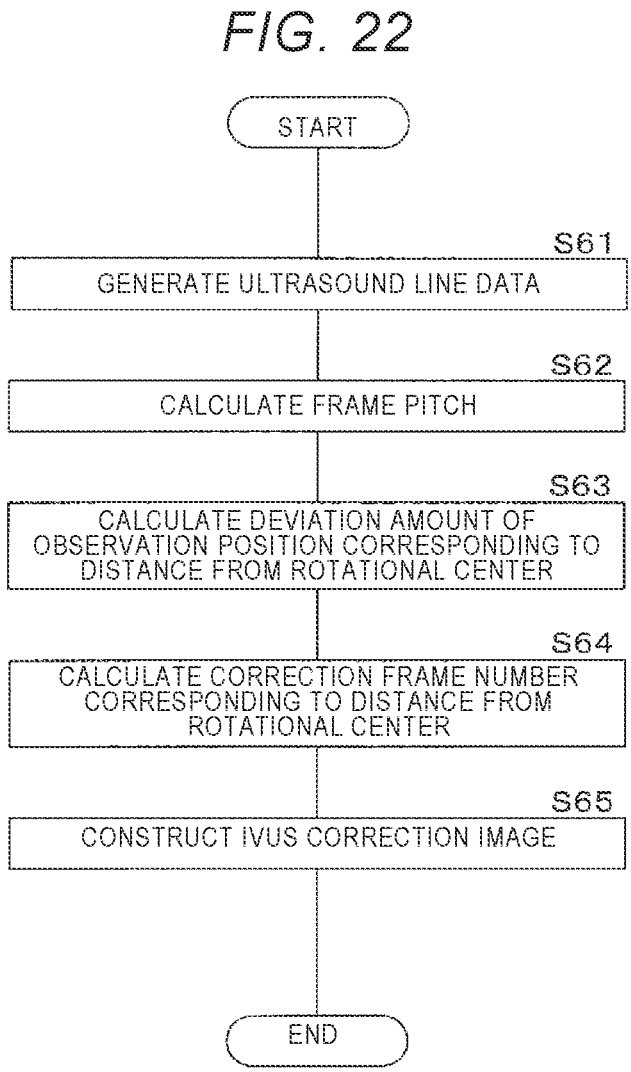
FIG. 22 is a flowchart showing an example of a tomographic image correction processing procedure in Embodiment 5.

FIG. 22 is a flowchart showing an example of a tomographic image correction processing procedure in Embodiment 5. It is assumed that the distance y between the IVUS sensor 12a and the marker 12c, and the ultrasound transmission and reception angle α of the IVUS sensor 12a shown in FIG. 19 are stored in the main storage unit 32 or the auxiliary storage unit 34.

When the intravascular imaging processing is started by the intravascular examination device 101, the control unit 31 of the image processing device 3 acquires the reflected wave data of the ultrasound from the IVUS sensor 12a via the MDU 2, and generates the ultrasound line data from the acquired reflected wave data of the ultrasound (S61). Next, the control unit 31 calculates a frame pitch at the time of imaging by the sensor portion 12 (S62). The calculation of the frame pitch is the same as S13 in FIG. 8. Next, the control unit 31 calculates a deviation amount of the observation position of the IVUS sensor 12a with respect to the position of the marker 12c at each distance from the rotational center of the sensor portion 12 (S63). A deviation amount $\Delta y$ (unit: mm) of the observation position in an area where the distance from the rotational center of the sensor portion 12 is L is calculated using the following Equation 7. y (unit: mm) is the distance between the IVUS sensor 12a and the marker 12c in the axial direction.

$$\Delta y = y - \Delta x_{IVUS} = y - L \times \cot \alpha \qquad \text{(Equation 7)}$$

Next, the control unit 31 calculates a correction amount (correction frame number) in the axial direction at each distance from the rotational center of the sensor portion 12 based on the respective deviation amounts of the observation positions of the IVUS sensor 12a with respect to the marker 12c (S64). The correction frame number is calculated using the following Equation 8 based on the deviation amount of the observation position calculated in S63 and the frame pitch calculated in S62.

$$\text{Correction frame number} = \Delta y / \text{frame pitch} \qquad \text{(Equation 8)}$$

In the present embodiment, the control unit 31 may also calculate the distance L from the rotational center of each location where the deviation amount $\Delta y$ is a multiple of the frame pitch, instead of calculating the deviation amount $\Delta y$ at each distance from the rotational center of the sensor portion 12. For example, when the frame pitch is 0.1 mm, each distance L is calculated at which the deviation amount $\Delta y$ of the observation position is 0.1 mm, 0.2 mm, 0.3 mm, . . . . In this case, 1, 2, 3, . . . can be specified as the correction frame number corresponding to each calculated distance L.

The control unit 31 constructs an IVUS correction image in which the observation target is matched with the position of the marker 12c based on the correction frame number corresponding to each distance calculated in S64 (S65). For example, the control unit 31 uses the ultrasound line data to synthesize each area in the IVUS images of a plurality of frames according to the correction frame number corresponding to the distance from the rotational center of the sensor portion 12, thereby constructing the IVUS correction image of one frame. In the example shown in FIGS. 20 and 21, the IVUS correction image of one frame is constructed by assigning each pixel value based on the data value corresponding to the area of the ultrasound line data of the (n−2)th frame to (n+2)th frame in order of the area far from the rotational center of the sensor portion 12. The control unit 31 performs the above-described correction processing, and interpolates the pixels between the lines by interpolation processing on the ultrasound line data to construct a two-dimensional IVUS image (IVUS correction image). The IVUS correction image constructed in this way is an IVUS image obtained by setting the contrast enhancement range of the marker 12c as an imaging object, so that an IVUS correction image obtained by imaging the location of the marker 12c on the angiographic image can be provided. The imaging position on the IVUS correction image and the position of the marker 12c on the angiographic image are matched in this way, and therefore, a relatively easy-to-interpret IVUS image can be provided, and an improvement in the accuracy of the procedure performed while confirming the IVUS image can be expected. The IVUS correction image constructed by the above-described processing can be displayed on, for example, the display apparatus 4 and presented to an operator using the image diagnosis catheter 1.

In the present embodiment, the same effects as those in the above-described embodiments can be obtained. In addition, in the present embodiment, since the IVUS correction image in which the observation target is matched with the marker 12c on the angiographic image can be obtained, it is possible to present a relatively easy-to-interpret IVUS image even when the image diagnosis apparatus 100 is used in a mode for acquiring only the IVUS image. In the present embodiment, it is also possible to construct an OCT correction image in which an observation target is matched with the marker 12c on the angiographic image by similar processing. In this case, it is possible to present a relatively easy-to-interpret OCT image even when the image diagnosis apparatus 100 is used in a mode for acquiring only the OCT image.

The configuration of the present embodiment can also be applied to the image diagnosis apparatus 100 of Embodiments 2 and 3, and similar effects also can be obtained when such a configuration is applied to Embodiments 2 and 3. When such a configuration is applied to Embodiments 2 and 3, each piece of information used in the correction processing (the distance y between the IVUS sensor 12a and the marker 12c, and the angle $\alpha$ of the ultrasound transmission and reception of the IVUS sensor 12a) is obtained by reading the code C applied to the image diagnosis catheter 1 or by acquiring from the server 6. In the present embodiment, it is also possible to apply modifications described as appropriate in the above-described embodiments.

The image processing device 3 of the above-described Embodiments 1 to 4 performs the correction processing of matching the observation position of the IVUS sensor 12a and the observation position of the OCT sensor 12b. In addition, for example, as in Embodiment 5, the observation position of the IVUS sensor 12a and the observation position of the OCT sensor 12b may be matched by performing correction processing of matching the observation positions to the position (contrast enhancement range) of the marker 12c on the IVUS image and the OCT image, respectively. In this case, even when the IVUS image acquisition processing and the OCT image acquisition processing are performed separately, for example, it is also possible to match the observation targets in the IVUS image and the OCT image by executing the correction processing of matching the observation positions with the position of the marker 12c for the obtained IVUS image and the obtained OCT image, respectively.

In each configuration of the above-described embodiments, the IVUS sensor 12a that captures an intravascular tomographic image using ultrasound and the OCT sensor 12b that captures an intravascular tomographic image using near-infrared light are used, but these embodiments are not limited to such a configuration. For example, a configuration also can be used in which instead of the IVUS sensor 12a or the OCT sensor 12b, various sensors capable of observing a condition of the blood vessel, such as a sensor that receives Raman scattered light from the inside of the blood vessel and captures an intravascular tomographic image, and a sensor that receives excitation light from the inside of the blood vessel and captures an intravascular tomographic image, are used.

The detailed description above describes embodiments of a program, an image processing method, and an image processing device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium storing a computer program that causes a computer to execute a process comprising:

acquiring a signal data set by a first inspection wave emitted in a direction inclined at a first angle with respect to a direction on a proximal end side on a longitudinal axis of a shaft of an imaging core of a catheter; and constructing an image obtained by using a direction inclined at a second angle with respect to a direction on a distal end side on the longitudinal axis of the shaft of the imaging core of the catheter, and wherein the second angle is different from the first angle with respect to the longitudinal axis as an observation target, based on the acquired signal data set.

2. The non-transitory computer-readable medium according to claim 1, wherein the imaging core includes a first transmitter and receiver configured to emit the first inspection wave and to receive a reflected wave of the first inspection wave, and a second transmitter and receiver configured to emit a second inspection wave in the direction inclined at the second angle with respect to the longitudinal axis and to receive a reflected wave of the second inspection wave, and the process further comprises:

constructing an image obtained by using the direction in which the second inspection wave is emitted as an observation target, based on the signal data set by the first inspection wave.

3. The non-transitory computer-readable medium according to claim 2, further comprising:

performing, based on an angular difference in a circumferential direction using the longitudinal axis as an axis between a direction in which the first transmitter and receiver emits the first inspection wave and the direction in which the second transmitter and receiver emits the second inspection wave, correction for eliminating the angular difference in the circumferential direction on the signal data set by the first inspection wave or a signal data set by the second inspection wave.

4. The non-transitory computer-readable medium according to claim 2, further comprising:

associating signal data included in the signal data set by the first inspection wave with signal data included in a signal data set by the second inspection wave, based on the first angle, the second angle, and a distance in the longitudinal axis between arrangement positions of the first transmitter and receiver and the second transmitter and receiver provided in the imaging core; and constructing an image obtained by using the direction in which the second inspection wave is emitted as an observation target, based on the associated contents and the signal data set by the first inspection wave.

5. The non-transitory computer-readable medium according to claim 2, further comprising:

acquiring the first angle and the second angle measured when manufacturing the catheter, and a distance in the longitudinal axis between arrangement positions of the first transmitter and receiver and the second transmitter and receiver of the imaging core; and constructing an image obtained by using the direction in which the second inspection wave is emitted as an observation target, based on the acquired first angle, the acquired second angle, and the acquired distance in the longitudinal axis, and the signal data set by the first inspection wave.

6. The non-transitory computer-readable medium according to claim 2, further comprising:

calculating a distance in the longitudinal axis between an emitting position of the first inspection wave and an emitting position of the second inspection wave at each distance from the imaging core to an observation target, based on the first angle, the second angle, and a distance in the longitudinal axis between arrangement positions of the first transmitter and receiver and the second transmitter and receiver of the imaging core;

calculating a correction amount for constructing an image obtained by using the direction in which the second inspection wave is emitted as an observation target, based on the calculated distance between the emitting positions, an emitting interval of the first inspection wave, and the signal data set by the first inspection wave; and constructing an image obtained by using the direction in which the second inspection wave is emitted as an observation target, based on the calculated correction amount and the signal data set by the first inspection wave.

7. The non-transitory computer-readable medium according to claim 2, further comprising:

inputting, when the signal data set by the first inspection wave and a signal data set by the second inspection wave are input, the acquired signal data set by the first inspection wave and the acquired signal data set by the second inspection wave to a training model, which is trained to output the first angle, the second angle, and a distance in the longitudinal axis between arrangement positions of the first transmitter and receiver and the second transmitter and receiver of the imaging core, to specify the first angle, the second angle, and the distance in a direction of the longitudinal axis; and constructing an image obtained by using the direction in which the second inspection wave is emitted as an observation target, based on the specified first angle, the specified second angle, the specified distance in the direction of the longitudinal axis, and the signal data set by the first inspection wave.

8. The non-transitory computer-readable medium according to claim 1, wherein the imaging core includes a first transmitter and receiver configured to emit the first inspection wave and to receive a reflected wave of the first inspection wave, and a contrast marker formed of an X-ray opaque material, and the process further comprises:

associating signal data included in the signal data set by the first inspection wave with an X-ray image obtained by imaging the contrast marker, based on a distance in the longitudinal axis between arrangement positions of the first transmitter and receiver and the contrast marker provided on the imaging core, and the first angle; and constructing an image obtained by using a contrast enhancement range of the contrast marker in the X-ray image as an observation target, based on the associated contents and the signal data set by the first inspection wave.

9. An image processing method executed by a computer, the method comprising:

acquiring a signal data set by a first inspection wave emitted in a direction inclined at a first angle with respect to a direction on a proximal end side on a longitudinal axis of a shaft of an imaging core of a catheter; and constructing an image obtained by using a direction inclined at a second angle with respect to a direction on a distal end side on the longitudinal axis of the shaft of the imaging core of the catheter, and wherein the second angle is different from the first angle with respect to the longitudinal axis as an observation target, based on the acquired signal data set.

10. The method according to claim 9, wherein the imaging core includes a first transmitter and receiver configured to emit the first inspection wave and to receive a reflected wave of the first inspection wave, and a second transmitter and receiver configured to emit a second inspection wave in the direction inclined at the second angle with respect to the longitudinal axis and to receive a reflected wave of the second inspection wave, and the method further comprises:

constructing an image obtained by using the direction in which the second inspection wave is emitted as an observation target, based on the signal data set by the first inspection wave.

11. The method according to claim 10, further comprising:

performing, based on an angular difference in a circumferential direction using the longitudinal axis as an axis between a direction in which the first transmitter and receiver emits the first inspection wave and the direction in which the second transmitter and receiver emits the second inspection wave, correction for eliminating the angular difference in the circumferential direction on the signal data set by the first inspection wave or a signal data set by the second inspection wave.

12. The method according to claim 10, further comprising:

associating signal data included in the signal data set by the first inspection wave with signal data included in a signal data set by the second inspection wave, based on the first angle, the second angle, and a distance in a direction of the longitudinal axis between arrangement positions of the first transmitter and receiver and the second transmitter and receiver provided in the imaging core; and constructing an image obtained by using the direction in which the second inspection wave is emitted as an observation target, based on the associated contents and the signal data set by the first inspection wave.

13. The method according to claim 10, further comprising:

acquiring the first angle and the second angle measured when manufacturing the catheter, and a distance in a direction of the longitudinal axis between arrangement positions of the first transmitter and receiver and the second transmitter and receiver of the imaging core; and constructing an image obtained by using the direction in which the second inspection wave is emitted as an observation target, based on the acquired first angle, the acquired second angle, and the acquired distance in the direction of the longitudinal axis, and the signal data set by the first inspection wave.

14. The method according to claim 10, further comprising:

calculating a distance in the longitudinal axis direction between an emitting position of the first inspection wave and an emitting position of the second inspection wave at each distance from the imaging core to an observation target, based on the first angle, the second angle, and a distance in a direction of the longitudinal axis between arrangement positions of the first transmitter and receiver and the second transmitter and receiver of the imaging core;

calculating a correction amount for constructing an image obtained by using the direction in which the second inspection wave is emitted as an observation target, based on the calculated distance between the emitting positions, an emitting interval of the first inspection wave, and the signal data set by the first inspection wave; and constructing an image obtained by using the direction in which the second inspection wave is emitted as an observation target, based on the calculated correction amount and the signal data set by the first inspection wave.

15. The method according to claim 10, further comprising:

inputting, when the signal data set by the first inspection wave and a signal data set by the second inspection wave are input, the acquired signal data set by the first inspection wave and the acquired signal data set by the second inspection wave to a training model, which is trained to output the first angle, the second angle, and a distance in a direction of the longitudinal axis between arrangement positions of the first transmitter and receiver and the second transmitter and receiver of the imaging core, to specify the first angle, the second angle, and the distance in the direction of the longitudinal axis; and constructing an image obtained by using the direction in which the second inspection wave is emitted as an observation target, based on the specified first angle, the specified second angle, the specified distance in the longitudinal axis, and the signal data set by the first inspection wave.

16. The method according to claim 9, wherein the imaging core includes a first transmitter and receiver configured to emit the first inspection wave and to receive a reflected wave of the first inspection wave, and a contrast marker formed of an X-ray opaque material, and the method further comprises:

associating signal data included in the signal data set by the first inspection wave with an X-ray image obtained by imaging the contrast marker, based on a distance in a direction of the longitudinal axis between arrangement positions of the first transmitter and receiver and the contrast marker provided on the imaging core, and the first angle; and constructing an image obtained by using a contrast enhancement range of the contrast marker in the X-ray image as an observation target, based on the associated contents and the signal data set by the first inspection wave.

17. An image processing device comprising:

a control unit configured to:

acquire a signal data set by a first inspection wave emitted in a direction inclined at a first angle with respect to a direction on a proximal end side on a longitudinal axis of a shaft of an imaging core of a catheter; and construct an image obtained by using a direction inclined at a second angle with respect to a direction on a distal end side on the longitudinal axis of the shaft of the imaging core of the catheter, and wherein the second angle is different from the first angle with respect to the longitudinal axis as an observation target, based on the acquired signal data set.

18. The image processing device according to claim 17, wherein the imaging core includes a first transmitter and receiver configured to emit the first inspection wave and to receive a reflected wave of the first inspection wave, and a second transmitter and receiver configured to emit a second inspection wave in the direction inclined at the second angle with respect to the longitudinal axis and to receive a reflected wave of the second inspection wave; and the control unit is configured to construct an image obtained by using the direction in which the second inspection wave is emitted as an observation target, based on the signal data set by the first inspection wave.

19. The image processing device according to claim 18, wherein the control unit is further configured to:

perform, based on an angular difference in a circumferential direction using the longitudinal axis as an axis between a direction in which the first transmitter and receiver emits the first inspection wave and the direction in which the second transmitter and receiver emits the second inspection wave, correction for eliminating the angular difference in the circumferential direction on the signal data set by the first inspection wave or a signal data set by the second inspection wave.

20. The image processing device according to claim 18, wherein the control unit is further configured to:

associate signal data included in the signal data set by the first inspection wave with signal data included in a signal data set by the second inspection wave, based on the first angle, the second angle, and a distance in a direction of the longitudinal axis between arrangement positions of the first transmitter and receiver and the second transmitter and receiver provided in the imaging core; and construct an image obtained by using the direction in which the second inspection wave is emitted as an observation target, based on the associated contents and the signal data set by the first inspection wave.

\* \* \* \* \*